United States Patent
Wang et al.

(10) Patent No.: US 12,207,939 B2
(45) Date of Patent: Jan. 28, 2025

(54) ASSESSING TREATMENT RESPONSE WITH ESTIMATED NUMBER OF TUMOR CELLS

(71) Applicants: University of Cincinnati, Cincinnati, OH (US); Children's Hospital Medical Center, Cincinnati, OH (US)

(72) Inventors: Jinghua Wang, Mason, OH (US); Lili He, Mason, OH (US)

(73) Assignees: University of Cincinnati, Cincinnati, OH (US); Children's Hospital Medical Center, Cincinnati, OH (US)

( * ) Notice: Subject to any disclaimer, the term of this patent is extended or adjusted under 35 U.S.C. 154(b) by 431 days.

(21) Appl. No.: 17/777,450

(22) PCT Filed: Oct. 20, 2020

(86) PCT No.: PCT/US2020/056425
§ 371 (c)(1),
(2) Date: May 17, 2022

(87) PCT Pub. No.: WO2021/108043
PCT Pub. Date: Jun. 3, 2021

(65) Prior Publication Data
US 2023/0360217 A1   Nov. 9, 2023

Related U.S. Application Data

(60) Provisional application No. 62/941,116, filed on Nov. 27, 2019.

(51) Int. Cl.
*A61B 5/00* (2006.01)
*G06T 7/00* (2017.01)
(Continued)

(52) U.S. Cl.
CPC .......... *A61B 5/4848* (2013.01); *G06T 7/0016* (2013.01); *G06T 7/45* (2017.01);
(Continued)

(58) Field of Classification Search
None
See application file for complete search history.

(56) References Cited

U.S. PATENT DOCUMENTS 8,880,146 B1   11/2014   Schepkin et al.
9,309,564 B2   4/2016    Depinho
(Continued)

FOREIGN PATENT DOCUMENTS

WO   2018222979 A1   12/2018
WO   2019134896 A1   7/2019
(Continued)

OTHER PUBLICATIONS

International Search Report and Written Opinion mailed Jan. 26, 2021 in reference to co-pending application No. PCT/US2020/056425 filed Oct. 20, 2020.
(Continued)

*Primary Examiner* — Leon Flores
(74) *Attorney, Agent, or Firm* — Dinsmore & Shohl LLP

(57) ABSTRACT

A method or system for assessing a patient response to a cancer treatment is provided. The method or system includes acquiring at least one base-line radiological image related to a patient immediately before a treatment, acquiring at least one follow-up radiological image during or after the treatment at a predetermined time interval, estimating a first number of specific tumor cells in a region of interest of the patient based on image features of the base-line radiological image using an algorithm or a model, estimating a second number of specific tumor cells in the region of interest of the patient based on image features of the follow-up radiological image using the algorithm or the model, obtaining a difference between the first number of specific tumor cells and the second number of specific tumor cells, and classifying a treatment response to a cancer based on the difference.

20 Claims, 10 Drawing Sheets

(51) Int. Cl.
  *G06T 7/45* (2017.01)
  *G06T 7/62* (2017.01)
  *G06V 10/44* (2022.01)
  *G06V 10/82* (2022.01)
  *G06V 20/69* (2022.01)
(52) U.S. Cl.
  CPC .............. *G06T 7/62* (2017.01); *G06V 10/454* (2022.01); *G06V 10/82* (2022.01); *G06V 20/695* (2022.01); *G06T 2207/10064* (2013.01); *G06T 2207/10081* (2013.01); *G06T 2207/10088* (2013.01); *G06T 2207/10104* (2013.01); *G06T 2207/10116* (2013.01); *G06T 2207/10132* (2013.01); *G06T 2207/20076* (2013.01); *G06T 2207/20081* (2013.01); *G06T 2207/20084* (2013.01); *G06T 2207/30016* (2013.01); *G06T 2207/30096* (2013.01); *G06T 2207/30242* (2013.01)

(56) References Cited

U.S. PATENT DOCUMENTS

| | | | |
|---|---|---|---|
| 9,370,304 | B2 | 6/2016 | Cao et al. |
| 9,655,563 | B2 | 5/2017 | Liu et al. |
| 9,726,669 | B2 | 8/2017 | Kim et al. |
| 9,889,318 | B2 | 2/2018 | Dempsey |
| 9,952,300 | B2 | 4/2018 | Giavazzi et al. |
| 9,963,747 | B2 | 5/2018 | Bryant et al. |
| 10,023,916 | B2 | 7/2018 | Frendewey et al. |
| 10,383,960 | B2 | 8/2019 | Williamson et al. |
| 2010/0284927 | A1 | 11/2010 | Lu et al. |
| 2013/0329973 | A1 | 12/2013 | Cao et al. |
| 2017/0356976 | A1 | 12/2017 | Shapiro et al. |
| 2018/0087114 | A1 | 3/2018 | Melnikova et al. |
| 2018/0298447 | A1* | 10/2018 | Fleischhacker ...... C12Q 1/6886 |
| 2019/0032151 | A1 | 1/2019 | Wallin et al. |
| 2019/0180139 | A1 | 6/2019 | Leor et al. |
| 2019/0209572 | A1 | 7/2019 | Spiegel et al. |
| 2019/0343476 | A1 | 11/2019 | Smith |
| 2019/0346448 | A1 | 11/2019 | Crudgington et al. |

FOREIGN PATENT DOCUMENTS

| | | |
|---|---|---|
| WO | 2019200252 A1 | 10/2019 |
| WO | 2020131699 A3 | 6/2020 |

OTHER PUBLICATIONS

Yin et al., "Tumor Cell Load and Hetergeneity Estimation From Diffusion-Weighted MRI Calibrated With Histological Data: an Example from Lung Cancer", IEEE Trans Med. Imaging, vol. 37, Issue 1, pp. 35-46, Apr. 27, 2017.

Chakraborty, "EC3: Combining Clustering and Classification for Ensemble Learning", Journal of Latex Class Files, vol. 13, No. 9, pp. 781-786, Journal of Latex Class Files, Sep. 30, 2014.

Namikawa, et al., "Prediction of additional lymph node positivity and clinical outcome of micrometastases in sentinel lymph nodes in cutaneous melanoma: A multi-institutional study of 450 patient in Japan", The Journal of Dermatology, vol. 39, Issue 2, pp. 130-137, Sep. 28, 2011.

\* cited by examiner

ASSESSING TREATMENT RESPONSE WITH ESTIMATED NUMBER OF TUMOR CELLS

CROSS-REFERENCE TO RELATED APPLICATIONS

This application is a national phase of International Application No. PCT/US2020/056425 filed on Oct. 20, 2020, which claims the benefit of U.S. Provisional Application No. 62/941,116 filed on Nov. 27, 2019, the entire contents of which are herein incorporated by reference.

FIELD OF THE INVENTION

The present application generally relates to the use of image biomarkers for quantify the cancer cells to assess treatment response in cancer. More particularly, the present application relates to cancer treatment response and detect the recurrence of primary brain tumor and brain metastases.

BACKGROUND

There are more than 18 million cancer cases and over 8 million people die of cancer around the world each year. The global market for cancer therapies is projected to reach US $220. 5 billion by 2025. This high mortality rate is mainly due to late detection of the disease and treatment assessment. Early and accurate treatment assessment is very important in clinical practices and the development of anti-cancer drugs as well as treatment techniques. If the assessment suggests that current therapy is ineffective, one will escalate therapy, change therapy or adjust the dose of therapy. On the contrary, one will minimize or stop the therapy timely if the assessment indicate that current therapy is effective. Both patients, healthcare system and pharmaceutical company can benefit from the early and accurate treatment assessment. The early and accurate treatment assessment can improve patient management, reduce side effect, improve the patient quality of life, save lives of patients, and minimize the cost of healthcare. As for pharmaceutical company, the accurate and early treatment assessment enables to reduce drug development time, improve drug efficacy, increase successful rate in clinical trials, and save the cost for anti-cancer drug development.

Currently, the methods for treatment assessment includes invasive surgical biopsy and minimally invasive or non-invasive methods. Surgical biopsy is a gold standard to assess the treatment effectiveness. The treatment assessment of cancer is performed by estimating changes in the number of cancer cells that are extracted from biopsy tissue. However, surgical biopsy often is complex, invasive, costly, risky, and sometimes unfeasible. Additionally, surgical biopsy only reflects a subpopulation of the tumor cells, creating sampling bias. The minimally invasive or non-invasive methods include liquid biopsy and medical imaging. Liquid biopsies are relatively simple to obtain, making them less invasive and less expensive. But it remains unknown if and to what degree liquid biopsy-based tests will contribute to diagnosis, treatment stratification, and follow-up monitoring. Non-invasive medical imaging is a cost-effective alternative to tumor biopsies when these biopsies are associated with significant risk, tumor tissue is insufficient or inaccessible, and/or serial assessment of tumor molecular abnormalities is needed to optimize treatment. Systems and/or methods for assessing therapy response are described in prior art:

U.S. Pat. No. 8,880,146 B1 to Victor D. Schepkin and Cathy W. Levenson discloses a safe and noninvasive assessment of tumor resistance using one diffusion or sodium MRI scan.

U.S. Pat. No. 9,370,304B2 to Cao Y et al discloses a method to identify physiological, metabolic, molecular, and/or biological imaging-defined abnormalities (phenotypes) of diseases for diagnosis, prognosis or prediction of therapy response and/or for intensified local treatment.

International Publication No. WO2006133420A2 and U.S. Pat. No. 9,963,747B2 to Barbara M. Bryant et al. disclose individual markers or marker sets for the identification, assessment, and treatment of patients with cancer therapy.

International Publication No. WO2007095186A2 and U.S. Pat. No. 9,309,564B2 to Ronald A. Depinho disclose compositions, kits, and methods for detecting, characterizing, preventing, and treating cancer.

International Publication No. WO2009055542 and U.S. Patent Application Publication No. 20100284927A1 to Zheng-Rong Lu et al. disclose methods for using macromolecular MRI contrast agents to evaluate the effectiveness of anti-cancer treatments over time.

International Publication No. WO2010132723A1 and U.S. Pat. No. 9,726,669B2 to Phillip Kim et al. disclose a method for detecting the tumor cells by circulating system for cancer diagnosis, prognosis, and in the design of cancer treatments.

International Publication No. WO2013057697A1 and U.S. Patent Application Publication No. 20190180139A1 to Zach L et al. disclose a method of producing magnetic resonance (MR) maps and, more particularly, but not exclusively to using such maps to identify and study cancers, particularly but not necessarily brain cancers.

International Publication No. WO2013131884A1 and U.S. Pat. No. 9,952,300B2 to Raffaella Giavazzi et al. disclose paramagnetic contrast agents and a Dynamic Contrast Enhanced-MRI method for assessing the delivery of a macromolecular anticancer drug or pro-drug within pathological tissues.

International Publication No. WO2014066853A1 and U.S. Pat. No. 9,889,318B2 to James F. Dempsey discloses changes in edema estimated by one or more MRI measurements.

International Publication No. WO2014172376A2 and U.S. patent Ser. No. 10/023,916B2 to David Frendewey et al. disclose compositions and methods for determining circulating biomolecules, and thereby becomes markers for evaluating tumor cell response to anti-cancer therapy.

International Publication No. WO2015048103A1 and U.S. Pat. No. 9,655,563B2 to David Liu et al. disclose a method for early therapy response assessment of lesions using machine learning. However, this method needs annotated ground truths. However, it is very difficult to get the labelled ground truths because cancer is dynamic and heterogeneous, particularly in the early stage of treatment. The ability to accurately assess a patient's response to treatment would allow physicians to adjust treatment course for maximum effectiveness. Therefore, there is an unmet need for noninvasive, rapid and accurate technology to assess therapeutic response in brain cancer.

International Publication No. WO2015061540A1 and U.S. patent Ser. No. 10/383,960 to Peter R. Williamson et al. disclose a new radioactive, isotopically-labeled calcofluor derivatives for the detection of fungi by positron emission tomography (PET).

International Publication No. WO2016141324A2 and U.S. Patent Application Publication No. 20180087114A1 to Vlada Melnikova and Mark G. Erlander disclose a method to determine responsiveness of a subject to a treatment for a cancer by the use of changes in cancer biomarker presence in bodily fluids before and during treatment to assess treatment efficacy.

International Publication No. WO2016179310A1 and U.S. Patent Application Publication No. 20190343476A1 to Andrew Dennis Smith disclose a computer-implemented method for determining and evaluating tumor treatment using cross-sectional images.

U.S. Patent Application Publication No. 20170356976A1 to Erik Shapiro et al. discloses a system and method for detecting magnetic-labeled substances into a subject using magnetic resonance imaging.

International Publication No. WO2017181079A2 and U.S. Patent Application Publication No. 20190032151A1 to Jeffrey Wallin and Priti Hegde disclose methods to treating cancer and monitor the response of a patient having an anti-cancer therapy that comprises an anti-VEGF antibody and an anti-PD-L1 antibody.

International Publication No. WO2018035424A1 and U.S. Patent Application Publication No. 20190209572 A1 to David A. Spiegel et al. disclose a bifunctional compounds which are useful in the treatment of fungal infections.

International Publication No. WO2019134896A1 to Wimberger-Friedl, Reinhold et al. discloses a computerized system for monitoring cancer therapy.

International Publication No. WO2019200252A1 to Velculescu V. E. and Anagnostou V discloses methods to determine the efficacy of an immunotherapy and resistance to an immunotherapy in a subject by detection of circulating tumor DNA (ctDNA) and/or differences in TCR clonotype levels.

International Publication No. WO2019217877A1 and U.S. Patent Application Publication No. 20190346448A1 to Allyson Crudgington et al. disclose compositions and methods for identifying cancer cells from liquid biopsy.

International Publication No. WO2020131699 to Maxim Brevnov and Elizabeth Rivers discloses methods for analyzing blood sample to determine copy number variation and aneuploidy in the context of circulating fetal cells, microdeletions, single nucleic acid variations associated with cancer, or early relapse of cancer and metastasis.

Assessing therapy response based on tissue specimens from patients is limited by a measurable tumor size, repeated surgical sampling and sampling bias. The technological advancements in liquid biopsy enable to provide provides a faster, clinically suitable, turnaround time with lower costs method to assess therapy response at molecular, genetic and cellular levels. However, liquid biopsy methods are challenging due to their extremely low concentration in blood, cerebral spinal fluid (CSF) and etc. During the past decade, the great efforts to develop consensus criteria for assessing response and progression in tumors, together with the development of the standardized tumor imaging protocol, have improved reliability and reduced variability in determining outcomes in oncology clinical trials. These consensus criteria are mainly conducted by measuring changes in tumor size several months after therapy has been performed. However, the known tumor response criteria is inconsistent, difficult to implement, narrowly tailored, expensive, and not reliably reproducible. Further, the effects of some newer anti-cancer treatment therapies are difficult to determine with the current tumor response criteria. Additionally, it is very difficult to distinguish pseudo-progression and pseudo-response from true progression of tumor therapy. The ability during the early stages of treatment to determine whether a treatment will be effective would provide an opportunity to optimize individual patient management and avoid unnecessary systemic toxicity, expense, and treatment delays. Therefore, early and accurate evaluation of cancer treatment response has an increasingly important role in managing patients with cancer since the evaluation could be crucial for timely change of therapy.

SUMMARY

It should be understood that the invention is not limited in its application to the following description or illustrated in the drawings. The invention is capable of other embodiments or of being practiced in various ways. Additionally, it should be understood that the terminology herein is for the purpose of description and should not be regarded as limiting.

To overcome the difficulties of assessing tumor response to various therapies based on the quantification of enhanced area, the present disclosure provides a method incorporating artificial intelligence capabilities to assess the actual tumor response based on the quantification of the number of post-treatment tumor cells, and provides earlier and more accurate treatment response assessment over what is currently available.

This disclosure describes method and system to assess therapeutic response in brain cancer by quantifying specific tumor cells from acquired images. It should be understood that the present method can be extended for other image modalities, such as computed tomography (CT), positron emission tomography (PET), X-ray, ultrasound, but not limited to, magnetic resonance spectroscopy (MRS), magnetic resonance spectroscopy imaging (MRSI), near-infrared (NIR) fluorescence imaging, nuclear medicine imaging, though example operations and example device are carried out for brain tumor magnetic resonance imaging (MRI).

In one embodiment, a method for assessing a patient response to a cancer treatment. The method includes acquiring at least one base-line radiological image related to a patient immediately before a treatment, acquiring at least one follow-up radiological image during or after the treatment at a predetermined time interval, classifying individual cells into cell subtypes in a region of interest of the patient based on image features of the base-line radiological image using a classifier model, estimating a first number of specific tumor cells in the region of interest of the patient based on classification of individual cells in the base-line radiological image, classifying individual cells into cell subtypes in the region of interest of the patient based on image features of the follow-up radiological image using the classifier model, estimating a second number of specific tumor cells in the region of interest of the patient based on classification of individual cells in the follow-up radiological image, obtaining a difference between the first number of specific tumor cells and the second number of specific tumor cells, and classifying a treatment response to a cancer based on the difference.

In another embodiment, a system for assessing a patient response to a cancer treatment is provided. The system includes a receiver configured to acquire at least one base-line radiological image related to a patient immediately before a treatment, and acquire at least one follow-up radiological image after the treatment at a predetermined time interval, and a processor configured to: classify individual cells into cell subtypes in a region of interest of the patient based on image features of the base-line radiological image using a classifier model, estimate a first number of specific tumor cells in a region of interest of the patient based on classification of individual cells in the base-line radiological image, classify individual cells into cell subtypes in the region of interest of the patient based on image features of the follow-up radiological image using the classifier model, estimate a second number of specific tumor cells in the region of interest of the patient based on classification of individual cells in the follow-up radiological image, calculate a difference between the first number of specific tumor cells and the second number of specific tumor cells, and classify a treatment response to a cancer based on the difference.

Alternatively or additionally, differentiating specific tumor cells from inflammatory cells in enhanced cells can be conducted by the image features of the acquired at least one image. Alternatively or additionally, variations in specific tumor cells before and after the treatments can be determined by the image features of the at least one image acquired after the treatment. It also can be determined by the comparison between the image features before and after the treatment.

In some implementations, the variation in enhanced cancer cells can be used as a criteria for response assessment of cancer therapies. This will push the existing response assessment from geometric change to cell number changes of a cancer. Compared with the conventional criteria, the present criteria are more accurate and hold a potential to avoid the side effects of the existing criteria, such as pseudo-progression and pseudo-response.

It should be understood that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

It is to be understood that this disclosure is not limited in its application to the details of construction and the arrangement of the components set forth in the following description or illustrated in the drawings. The invention is capable of other embodiments or of being practiced or carried out in various ways. Also, it is to be understood that the terminology employed herein is for the purpose of description and should not be regarded as limiting.

BRIEF DESCRIPTION OF THE DRAWINGS

The components in the drawings are not necessarily to scale relative to each other. Like reference numerals designate corresponding parts throughout the several views.

DETAILED DESCRIPTION

Figure 1:
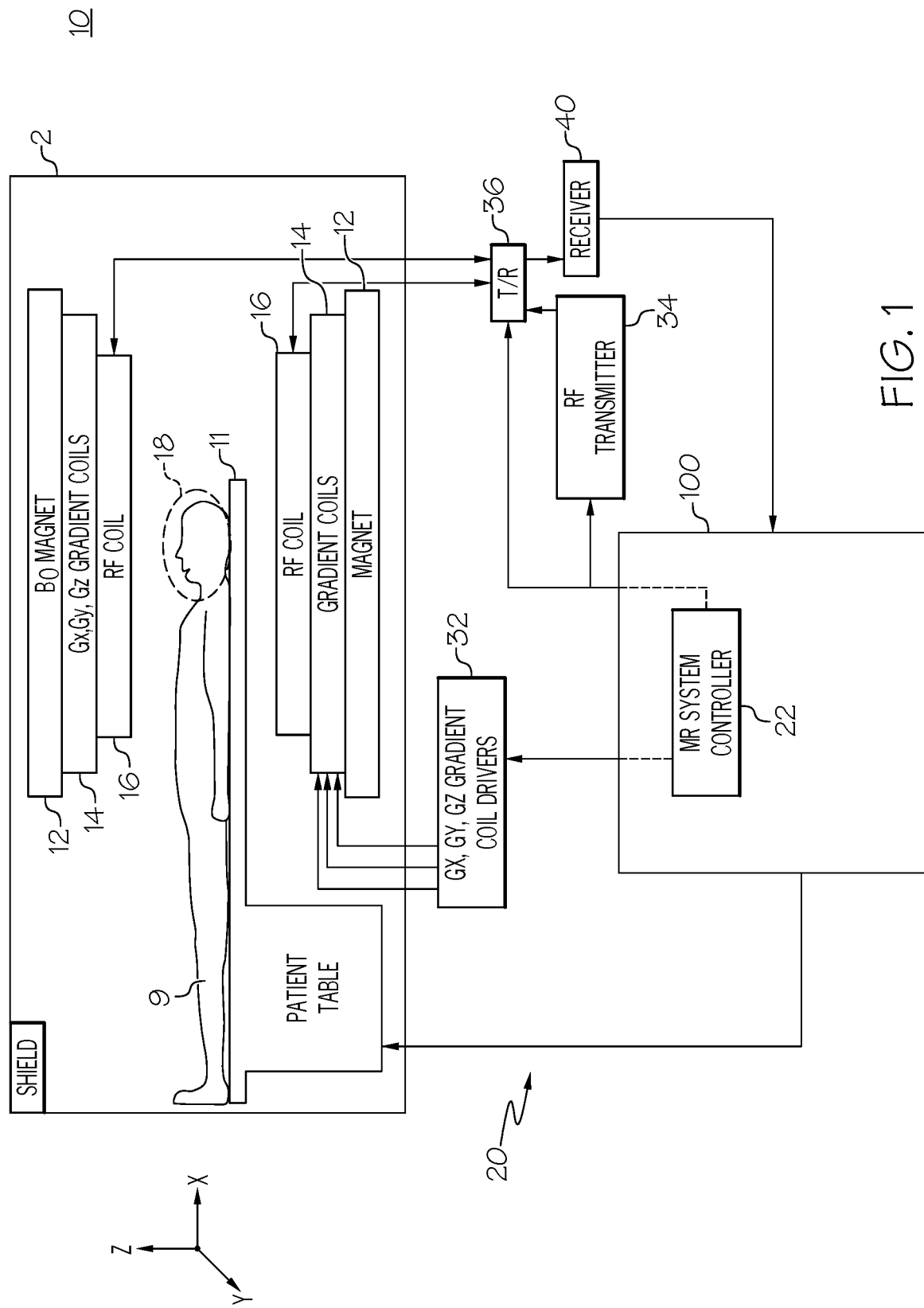
FIG. 1 is a diagram illustrating an example MRI system of image modalities, according to one or more embodiments shown and described herein.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise.

The term "comprising" and variations thereof as used herein are used synonymously with the term "including" and variations thereof and are open, non-limiting terms.

The terms "optional" or "optionally" used herein mean that the subsequently described feature, event or circumstance may or may not occur, and that the description includes instances where said feature, event or circumstance occurs and instances where it does not.

The term "sample" as used herein refers to a tissue sample. It includes a specimen or culture obtained from any source. The samples obtained from human include, but are not limited to blood products, such as plasma, serum and the like.

The term "subject", "patient" or "object" as used herein interchangeably, means any a human. In some embodiments, the subject may be a human subject at risk for developing or already having cancer The terms "cancer" and "tumor" as used interchangeably herein, refer to cell growth that spreads to surrounding tissues, though the word tumor simply refers to a mass and a cancer is a particularly threatening type of tumor. The cancer indicates the physiological or pathological condition in which a population of cells are characterized by unregulated cell growth. A tumor is not necessarily a cancer. In one embodiment, there is the coexistence of various cells in a tumor or cancer, such as transformed cells, myoepithelial cell, inflammatory cell, immunomodulatory cells, endothelial cells, vascular cells, stromal cells, and cancer stem cells.

The term "liquid biopsy" and variations thereof as used herein indicate a tool to detect molecules or cells in body fluids, such as peripheral blood, urine, saliva, cerebral spinal fluid, and breast milk.

The terms "therapy" and "treatment" as used interchangeably herein, refer to an intervention performed with the intention of improving a subject's status. For example, the term "Treatment" or "therapy" and their variation herein for cancer indicate inhibiting further cancer growth, and thereby causing shrinkage of a cancer. The treatment of cancer or cancer includes anti-cancer drug, surgery, chemotherapy, but not limit to, radiation therapy, hormonal therapy, immunotherapy, targeted therapy, stem cell transplants, precision medicine and their combinations.

The term "radiological image" as used herein refers to image obtained from radiological imaging modalities which is different from the image obtained from histopathological image modalities. The radiological image are obtained from at least one of the imaging modalities consisting of magnetic resonance imaging (MRI), computed tomography (CT), positron emission tomography (PET), X-ray, ultrasound, magnetic resonance spectroscopy (MRS), magnetic resonance spectroscopy imaging (MRSI), near-infrared (NIR) fluorescence imaging, nuclear medicine imaging, and their variations.

The term "radiomics" as used herein is defined as the conversion of radiological images to higher dimensional image features and the subsequent mining of these data for medical practices. For example, the radiomics can identify tumor phenotype from anatomic or functional images at molecule or genetic or cellular levels by using the image features that are invisible by the naked eyes, including first and higher order statistics, fractal and shape features.

The term "radiogenomics" as used herein refers to the relationship between the imaging characteristics of a disease and its gene expression patterns, gene mutations, and other genome-related characteristics. Radiogenomics has a potential to study the cancer genomics without using invasive biopsy such as a surgery specimen.

The term "solid tumor" as used herein refers to abnormal mass of tissue with uncontrolled division of cells that usually does not contain cysts or liquid areas, wherein solid tumor includes, but not limit to, one or more of lung cancer, ovarian cancer, melanoma, breast cancer, prostate cancer, pancreatic cancer, colon cancer, hepatic cancer, head and neck cancers, genitourinary cancers, skin cancer, kidney cancer, thyroid cancer, pituitary cancer, bladder cancer primary brain cancer and brain metastases.

The terms "volume" and "number" of the cells as used interchangeably herein because we assume the density of the same cells is identical.

The term "cell" as used herein refers to living and/or died cells, most preferably to human cells. For example, cell includes one or more of a tissue cell, but not limited to, a tumor cell, the same tumor cells with different gene expressions, a died cell. Classic bulk sequencing data of tumor samples taken during surgery are always a mixture of tumor, normal tissue cells (including leukocytes, fibroblasts, and endothelial cells), and other cells (such as infiltrating immune cells).

The term "active cancer or tumor cells" as used herein is characterized by at least one of pathological features. For example, active cancer cells in brain metastases can characterized by blood brain barrier disruption. After the contrast agent administration, the contrast agent will leak into active cancer cells from capillaries and then enhance contrast enhanced magnetic resonance imaging (CE-MRI) signal intensity of active cancer cells. CE-MRI enhancement of active cancer cells is independent of treatment.

Inflammatory cell infiltration occurs when inflammatory cells such as neutrophils, eosinophils, lymphocytes, plasmacytes, macrophages and mast cells infiltrate around the blood vessels (perivascular infiltration). Inflammatory cells are a source of cytokines and growth factors that may target the endothelial cells and contribute to the development of structural and functional abnormalities of the vessel wall. The term "inflammatory cells" as used herein refer to the cells that relate with specific image features. For example, the inflammatory cells depend on the leakage of contrast agent in CE-MRI: Before cancer treatment, the contrast agent will not leak into inflammatory cells from capillaries and will not enhance CE-MRI signal intensity after the contrast agent administration. During or after the treatment, however, some cancer therapies (e.g., radiation therapy, immunotherapy and chemotherapy) enhance CE-MRI signal intensity of inflammatory cells. Therefore, it is very important to differentiate inflammatory cells and tumor cells in treatment assessments because the inflammatory cells may cause false positive response assessment of treatments.

The term "tumor microenvironment" as used herein refers to a set of variables, such as blood vessel density, and extracellular matrix stiffness, which contribute to the overall conditions that the cancer cells need to thrive in and migrate through.

The term "radiomic features" as used herein refers to apply quantitative features (i.e., shape, size, and textural patterns, etc.) of radiographic images to describe the characterization of biology at molecular, genetic and cellular levels, more specify in cancer biology. For example, the MM images have been used to identify HER2+ breast cancer brain metastases subtype for targeted. Moreover, the radiomic features obtained from contrast enhanced MRI, which is the most common modality of assessing brain tumor, can associate with peri-tumor edema or hemorrhage, adjacent bone, blood vessels, fat, or cerebrospinal fluid. Good selection of radiomic features can filter the characterization of these non-tumor cells and extract the characterization of tumor cells.

The term "tumor heterogeneity" as used herein refers the tumor of patients or the same patient that is composed of the cells with distinct molecular, genetic and cellular phenotypic features. It can further divided into inter-tumor heterogeneity (from different patients) and intra-tumor heterogeneity (from the same patients). For example, genetic heterogeneity of glioblastoma multiforme may involve isocitrate dehydrogenase (IDH)-mutant and IDH-wild in either different patients or the same patient.

The term "inter-tumor heterogeneity" as used herein refers to the tumors of the different patients that are composed of cells with distinct molecular, genetic and cellular phenotypic features.

The term "intra-tumor heterogeneity" as used herein refers to the tumor of a patient that is composed of cells with distinct molecular, genetic and cellular phenotypic features. The intra-tumor heterogeneity is further divided into inter-site heterogeneity (among different tumor sites) and intra-site heterogeneity (in a single tumor site).

The term "artificial intelligence (AI)" as used herein refers to a computer performing tasks commonly associated with human intelligence. Humans can code and program a computer based on an algorithm or model to conduct the computer how to act, reason, and learn.

The term "Cluster analysis or clustering" as used herein refers to is the task of grouping a set of objects in such a way that objects in the same group (called a cluster) are more similar (in some sense) to each other than to those in other groups (clusters). It is a main task of exploratory data mining, and a common technique for statistical data analysis, used in many fields, including pattern recognition, image analysis, information retrieval, bioinformatics, data compression, computer graphics and machine learning.

The term "machine learning" as used herein refers to a type of AI that sample data, known as "training data", are used to develop an algorithm or model in order to make predictions or decisions. Generally, the more data a machine learning model is exposed to, the better it performs over time.

The term "deep learning" as used herein refers to a subset of machine learning based on artificial neural networks model. A well-designed and well-trained deep learning model can perform various tasks classification tasks with higher accuracy and better performance.

The term "cancer pseudo-progression" as used herein corresponds to an increase of lesion size related to treatment, which is defined as a new or enlarging area(s) of contrast agent enhancement occurring early after the end of cancer therapy, in the absence of true cancer growth, which subsides or stabilizes without a change in therapy.

The term "cancer progression" as used herein is characterized by increased growth speed and invasiveness of the cancer cells. As a result of the progression, phenotypical changes occur and the cancer becomes more aggressive and acquires greater malignant potential.

The term "hyper progression" as used herein refers to an accelerated tumor growth after immune checkpoint inhibitors treatment with an increase in the absolute mass of tumor cells superior to what is expected in the setting of conventional progression on treatment. Generally, the tumor growth rate of hyper progression is more than a two-fold increase after initiation of immune checkpoint inhibitors therapy.

The term "response assessment criteria" as used herein is a set of published rules that define when cancers in cancer patients improve ("respond"), stay the same ("stabilize"), or worsen ("progress") during treatment. The criteria were published by an international collaboration including the European Organization for Research and Treatment of Cancer (EORTC), National Cancer Institute of the United States, and etc.

MRI System Overview

FIG. 1 depicts an MRI system 10, according to one or more embodiments described and shown herewith. In embodiments, the MRI system 10 shown in FIG. 1 includes a patient table 11, a static magnetic field generating unit 12, a gradient magnetic field generating unit 14 for generating respective magnetic fields in proximity to a target area 18 of an object 9, a transmitting and receiving unit 16, and a computing device 100. The patient table 11, the static magnetic field generating unit 12, the gradient magnetic field generating unit 14, and the transmitting and receiving unit 16 are placed within MRI RF shielding area 2 where noise of radio frequency is prevented from entering.

The static magnetic field generating unit 12 includes a main magnet configured to generate a strong static magnetic field in proximity to the target area 18 of the object 9. The static magnetic field generating unit 12 may be arranged to surround the target area 18 of the object 9. For example, the static magnetic field generating unit 12 may be a cylindrical-shaped unit. The gradient magnetic field generating unit 14 includes gradient magnetic field coils for generating gradient magnetic fields in an x-axis direction, a y-axis direction, and a z-axis direction, which are orthogonal to each other. The gradient magnetic field generating unit 14 may be arranged to surround the target area 18 of the object 9. For example, the gradient magnetic field generating unit 14 may be a cylindrical-shaped unit.

In embodiments, the transmitting and receiving unit 16 may include a transmission coil and a receiving coil. The transmission coil irradiates RF pulses to the object 9 and the receiving coil receives MR signals generated by the object 9. In some embodiments, the transmitting and receiving unit 16 may include a transceiver coil having the functions of both the transmission coil and the receiving coil. The receiving coil may be composed of, for example, a so-called array coil in which, for example, a plurality of coil elements are disposed to detect the MR signals generated by the object 9. An RF transmitter 34 may control the transmission coil of the transmitting and receiving unit 16 to irradiate RF pulses. A receiver 40 may receive MR signals generated by the object 9 from the receiving coil of the transmission and receiving unit 16. The RF transmitter 34 and the receiver 40 may communicate with the transmitting and receiving unit 16 through a transmitter/receiver interface 36.

In embodiments, the MRI system 10 includes the computing device 100. The computing device 100 includes a MRI system controller 22. The MRI system controller 22 may control the operations of the gradient coil drivers 32 that activate the gradient coils of the gradient magnetic field generating unit 14. The MRI system controller 22 may also control the operations of the RF transmitter 34 that activates the RF coil of the static magnetic field generating unit 12. The computing device 100 may receive MR signals from the receiving coil of the transmission and receiving unit 16 and reconstruct an MRI image based on the received MR signals. The details of the computing device 100 will be further described with reference to FIG. 1A below.

In embodiment, the computing device 100 may be operably coupled to other components of the MRI system 10, for example, using by any medium that facilitates data exchange between the components of the MRI system 10 and the computing device 100 including, but not limited to, wired, wireless and optical links. For example, the computing device 100 may convert the MR signals received from the transmitting and receiving unit 16 into k-space data. The computing device 100 may generate MR image data from the k-space data with image reconstruction processing. In some embodiments, the techniques for improving image quality with optimal variable flip angles may optionally be implemented using the MRI system 10.

Example Computing Device

Figure 1A:
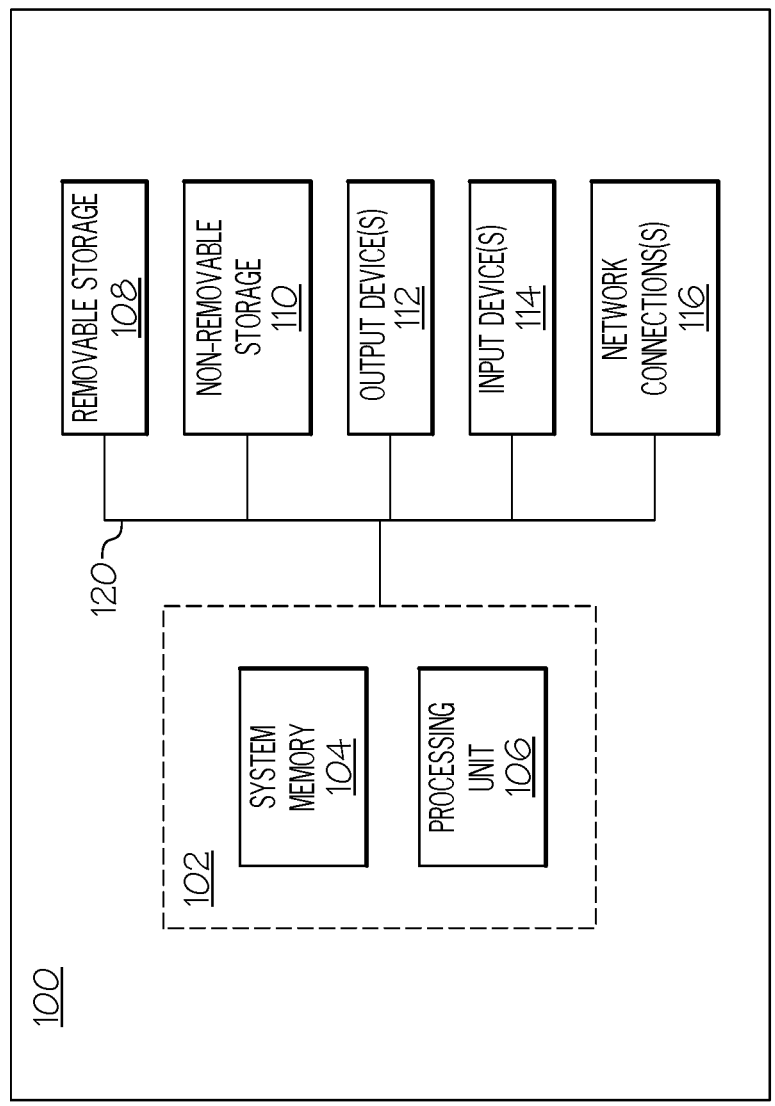
FIG. 1A is an example computing device, according to one or more embodiments shown and described herein.

FIG. 1A depicts a computing device 100 according to one or more embodiments shown and described herein. It should be appreciated that the logical operations described herein with respect to the various figures may be implemented (1) as a sequence of computer implemented acts or program modules (i.e., software) running on a computing device (e.g., the computing device described in FIG. 1A), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

It should be understood that the computing device 100 is only one example of a suitable computing environment upon which embodiments of the invention may be implemented. Optionally, the computing device 100 may be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In embodiments, the computing device 100 includes a controller 102 that includes one or more processing units 106 and one or more system memory modules 104. The controller 102 may be the same controller as the MRI system controller 22 in FIG. 1. In other embodiments, the controller 102 may be a separate controller from the MRI system controller 22 in FIG. 1.

Depending on the exact configuration and type of computing device, the one or more memory modules 104 may be volatile (such as random access memory (RAM)), non-volatile (such as read-only memory (ROM), flash memory, etc.), or some combination of the two. The one or more processing units 106 may be a standard programmable processor that performs arithmetic and logic operations necessary for operation of the computing device 100.

In embodiments, the computing device 100 includes communication path 120 that provides signal interconnectivity between various components of the computing device 100. Accordingly, the communication path 120 may communicatively couple any number of processing units 106 with one another, and allow the components coupled to the communication path 120 to operate in a distributed computing environment. Specifically, each of the components may operate as a node that may send and/or receive data. As used herein, the term "communicatively coupled" means that coupled components are capable of exchanging data signals with one another such as, for example, electrical signals via conductive medium, electromagnetic signals via air, optical signals via optical waveguides, and the like.

Accordingly, the communication path 120 may be formed from any medium that is capable of transmitting a signal such as, for example, conductive wires, conductive traces, optical waveguides, or the like. In some embodiments, the communication path 120 may facilitate the transmission of wireless signals, such as Wi-Fi, Bluetooth, Near Field Communication (NFC) and the like. Moreover, the communication path 120 may be formed from a combination of mediums capable of transmitting signals. In one embodiment, the communication path 120 comprises a combination of conductive traces, conductive wires, connectors, and buses that cooperate to permit the transmission of electrical data signals to components such as processors, memories, sensors, input devices, output devices, and communication devices. Accordingly, the communication path 120 may comprise a vehicle bus, such as for example a LIN bus, a CAN bus, a VAN bus, and the like. Additionally, it is noted that the term "signal" means a waveform (e.g., electrical, optical, magnetic, mechanical or electromagnetic), such as DC, AC, sinusoidal-wave, triangular-wave, square-wave, vibration, and the like, capable of traveling through a medium.

The one or more processing units 106 may be configured to execute program code encoded in tangible, computer-readable media. Tangible, computer-readable media refers to any media that is capable of providing data that causes the computing device 100 (i.e., a machine) to operate in a particular fashion. Various computer-readable media may be utilized to provide instructions to the one or more processing units 106 for execution. Example tangible, computer-readable media may include, but is not limited to, volatile media, non-volatile media, removable media and non-removable media implemented in any method or technology for storage of information such as computer readable instructions, data structures, program modules or other data. One or more system memory modules 104, a removable storage 108, and a non-removable storage 110 are all examples of tangible, computer storage media. Tangible, computer-readable recording media may include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In embodiments, the one or more processing units 106 may execute program code stored in the one or more system memory modules 104. For example, a bus may carry data to the one or more system memory modules 104, from which the one or more processing units 106 receive and execute instructions. The data received by the one or more system memory modules 104 may be optionally stored on the removable storage 108 or the non-removable storage 110 before or after execution by the processing unit 106.

In embodiments, the computing device 100 may include additional storage such as removable storage 108 and non-removable storage 110 including, but not limited to, magnetic or optical disks or tapes.

The computing device 100 may also have input device(s) 114 such as a keyboard, mouse, touch screen, etc. The input device may be manipulated by an operator to input signals to the MRI apparatus to set the imaging method group, the performing order, the imaging condition, and the like. The computing device 100 may also have output device(s) 112 such as a display, speakers, printer, etc. The output device 112 may output image data such as local image data, diagnosis image data using display, printer and other displayer. The additional devices may be connected to the bus in order to facilitate communication of data among the components of the computing device 100.

Computing device 100 may also contain network connection(s) 116 that allow the device to communicate with other devices. The network connection(s) 116 may be any device capable of transmitting and/or receiving data via a wireless network. Accordingly, the network connection(s) 116 may include a communication transceiver for sending and/or receiving data according to any wireless communication standard. For example, the network connection(s) 116 may include a chipset (e.g., antenna, processors, machine readable instructions, etc.) to communicate over wireless computer networks such as, for example, wireless fidelity (Wi-Fi), WiMax, Bluetooth, IrDA, Wireless USB, Z-Wave, ZigBee, or the like.

It should be understood that various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

In some embodiments, the computing device 100 may include a workflow setting unit, an imaging operation determining unit, and an image reconstruction unit. The workflow setting unit may be a program module stored in the system memory modules 104. The workflow setting unit sets a first workflow relating to the MRI examination by estimating an imaging time of each of the imaging methods in the performing order initially set by a scan plan. Further, the workflow setting unit sets a second workflow relating to the MRI examination by estimating a shortest performing order, by which an examination time necessary to sequentially perform a plurality of imaging methods constituting the imaging method group set by the input unit is minimized. The imaging operation determining unit determines whether an imaging operation during a main imaging is implemented according to the workflow. In embodiments, the workflow setting unit and/or the imaging operation unit may be implemented using hardware, software, and or a combination thereof.

The image reconstruction unit may include an MR signal storage unit, a signal processing unit, and an image data storage unit. The MR signal storage unit (e.g., memory) stores the MR signals, which are collected by the receiver unit of the transmitting and receiving unit 16. The signal processing unit has an image reconstruction processing unit and an image processing unit. The image reconstruction processing unit generates image data from the MR signal storage unit by image reconstruction processing, for example, performed by a Fourier transformation such as 2D FFT. When the MR signals to a three-dimensional region are collected, the image reconstruction processing unit of the signal processing unit generates volume data. Subsequently, the image processing unit generates three-dimensional image data such as volume rendering image data, surface rendering image data and the like or two-dimensional image data, multi planar reconstruction image data, and the like, because predetermined image processing is performed for the volume data generated by the image reconstruction processing unit. Then, the image data described above obtained by the signal processing unit are stored to the respective storage regions of the image data storage unit.

Treatment Assessments and Criteria Overview

There are more than 18 million cancer cases and over 8 million people die of cancer around the world each year. This high mortality rate is mainly due to late detection of the disease and treatment assessment. Thus, there is a need for accurate and efficient techniques for treatment response assessment and the detection of cancer recurrence. In the era of molecular medicine, additionally, there is great interest in understanding cancer development in order to identify new therapeutic targets because of vast difference in cancer patient outcomes. Tumor treatment often induces the intra-tumor heterogeneity and requires to provide up-to-date response evaluation at molecular, genetic and cellular levels that meets the needs of oncologists delivering personalized cancer care.

Histopathology is the most reliable "gold standard" method for assessing therapy response of cancers. However, surgical biopsy and liquid biopsy have certain limitations. First, it is an invasive procedure and is sometimes not feasible in eloquent areas or difficult to access locations. For example, it is very risk to perform surgical biopsy in brain. Second, tissue and liquid biopsy may not fully reflect the overall picture of the tumor, due to its heterogeneity. A biopsy from the same tumor could yield different information, and thus affect clinical decision-making for the patient. Particularly, in the early stage of treatment, mixed morphology consisting of both treatment effects and cancer emphasize limits the accuracy of surgery biopsy. It is sensitive to inherent sampling error. Third, histological examinations are extensive and costly. The procedure for histological examinations is time-consuming and labor-intensive. For example, conventional detection and treatment assessment of cancer or tumor can be performed by estimating changes in the number of cancer cells with tissue biopsy or a liquid biopsy. The biopsy procedure is invasive, as tumor cells must be extracted from biopsy tissue. A routine biopsy examination takes 3-7 days. There are also the added expenses of labor and equipment to perform the biopsy. Fourth, histological assessment is an operator-dependent. Fifth, it requires short interval clinical follow-up with imaging, which may delay and compromise disease management in an aggressive cancer. Sixth, it is impossible for histological examinations to perform in vivo non-invasive monitoring of the tissue changes. Seventh, liquid biopsy is limited by two major factors—(a) the molecules obtained from the liquid biopsy may be made by both tumor cells and normal (i.e., healthy) cells; (b) the quantities of molecules obtained from liquid biopsy is too small to detect. Finally, the biopsy is a complicated procedure, and not all patients may agree to undergo it.

In order to overcome the drawbacks of treatment assessments based on histological examinations, non-invasive imaging methods or tumor response criteria have been proposed to predict and/or evaluate the effects of anti-cancer therapies. Various response assessment criteria, including response evaluation criteria in solid tumors (RECIST), Macdonald criteria, response assessment for neuro-oncology (RANO) criteria, the immunotherapy response assessment for neuro-oncology (iRANO) criteria, and so on, have been developed based on non-invasive medical imaging. Compared with treatment assessment based on histological assessment, the imaging methods have the following advantages: (1) The image methods can provide a non-invasive, cheap, repeated and fully covered treatment assessment. (2) The imaging methods allow information to be obtained about the tissues within a few minutes. It is possible to develop real-time treatment assessments. By contrast, a routine histological examination takes several days.

Conventional response assessment methods and criteria for anti-cancer therapy consist of assessment of size, shape, patterns, signal intensity. They are often inconsistent and limited, difficult to implement, narrowly tailored, expensive, and not reliably reproducible. For example, the response assessment criteria are conducted based on geometric measures, such as the diameter or volume of lesions in various criteria (e.g., RECIST or RANO or iRANO, etc.). The accuracy and precision of treatment assessment strongly depend on the image acquisition modalities, imaging parameters, tumor shape, lesion distribution and etc. For example, when post-contrast MRI images are acquired with $T_1$-weighted MRI sequences based on spin echo and gradient echo for assessing therapy response, their difference in echo times will lead to the difference in geometric measures of enhanced tumor lesion. In addition, the conventional criteria require minimize measurable size of tumor (often more than 5.0 mm). It will take a long period of time for the clinicians to make a decision based on the geometric measures about whether the therapy is likely to succeed or not, only when the tumor size is more than minimize measurable size. Current treatment assessments with geometric measure have an inherent latency due to the delay between chemotherapy administration and detection of tumor geometric change.

It will take about four to six week interval to effectively identifying the treatment response. The delay will lead to the following drawbacks. First, the delay leads to higher side-effects for the patient and greater cost of the therapy drugs. For example, chemotherapy cannot target the cancer cells alone due to their inability to differentiate between normal or cancer cells. As a result, it can cause significant normal tissue toxicity that includes, but are not limited to, decreased erythrocyte, leukocyte, and platelet counts, nausea, vomiting, hair loss, and fatigue. Second, the delay leads to a delay for new treatment option. For example, clinicians thought that the therapy fails and new therapy strategy should be selected when cancer recurrence occurs. The ability of high-resolution contrast enhanced MRI can detect confidently the sub-millimeter tumor lesion. According to conventional response criteria, the sub-millimeter tumor lesion is thought as a non-measurable tumor lesion until the tumor lesion grow to more than 5.0 mm after several weeks or months.

Geometric measures according to conventional criteria may be inaccurate because many path-physiological factors can lead to the changes in geometric measures. For example, RANO criteria evaluates the treatment response mainly according to enhanced area. However, the enhanced area may be caused not only by tumor cells with blood-brain barrier disruption, but also by the inflammation of normal tissue cells. Therefore, it is very difficult to distinguish pseudo-progression and pseudo-response from actual tumor change. Most recently, advanced imaging techniques (such as diffusion weighted imaging, perfusion weighted imaging, and magnetic resonance spectroscopy) have been proposed for accurate response assessment. These methods show promise in being able to differentiate pseudo-progression from progression. However, these studies are relatively small, heterogeneous, and limited in number. Conventionally, a single response criteria may not be good enough for all type of solid tumors with different therapeutic classes.

The conventional response criteria and treatment assessment method cannot sufficiently accurate to assess a number of anti-cancer therapies. It is expected that a new and general response criteria and treatment assessment method can be developed to more accurately assess all anti-cancer therapies. For example, RANO and iRANO are proposed to assess the therapy response with traditional tumor therapy and immune-therapy, respectively. The development of therapy assessment method for solid tumors with different therapeutic classes will greatly simplify the procedure of therapy response assessment, including image acquisition, interpretation, and clinical decision making. Immune checkpoint inhibitors frequently induce a delayed tumor shrinkage or pseudo-progression that is distinct from most other anti-cancer therapies. Delayed tumor shrinkage can sometimes be preceded by transient enlargement due to immune cell infiltration. Therefore, follow-up response assessment every 6-12 weeks is recommended for iRECIST, depending on the frequency of treatment visits, as recommended for RECIST 1.1. Misinterpretation of scans could lead to inappropriate discontinuation of a potentially effective therapy, or conversely, an ineffective treatment could be continued hoping for a delayed response that never comes. Further, intra-tumor heterogeneity has impacts on characterization of actionable targets, treatment planning, and drug resistance. Modern oncology is shifting from empirical treatment strategies to personalized treatment models because therapy response and patient outcomes greatly associated with tumor information at molecular, genetic and cellular levels. Current treatment assessment and therapy response criteria based on the geometric measures cannot provide tumor characteristics at molecular, genetic and cellular levels for personalized medicine.

Despite extensive efforts, progress in tumor treatment has been disappointingly slow. There are many reasons for this lack of progress: (1) tumor complexity including molecular heterogeneity over space and time, intrinsic resistance to therapies, and redundant signaling pathways; (2) the lack of non-invasive and fast method to assess therapy response accurately at molecular and genetic levels; (3) the lack of reliable and widely accepted response criteria to identify more effective therapies in cancer; (4) the lack of techniques to detect the tumor or tumor recurrence at the early stages; The ability to determine whether a treatment will be effective at the early stage of treatment will optimize individual patient management and avoid unnecessary systemic toxicity, expense, and treatment delays. Therefore, early and accurate evaluation of cancer treatment response has an increasingly important role in managing patients with cancer since the evaluation could be crucial for timely change of therapy; (5) the lack of techniques to distinguish pseudo-progression and pseudo-response from true progression of tumor therapy. Some advanced imaging modalities, such as diffusion weighted imaging, perfusion imaging, magnetic resonance spectroscopy, and PET, are under investigation, none is yet widely accepted as being able to accurately identify the treatment response; and (6) the lack of timely techniques to monitor treatment response at molecular, genetic and cellular levels for optimal cancer patients' care. Recently, molecularly-targeted cancer treatments are emerging as the standard-of-care for cancer patients. The tumor therapies often introduce intra-tumor heterogeneity and drug resistance, limiting the successful treatments of the patients with cancers. It is an urgent need to monitoring tumor heterogeneity repeatedly and timely at molecular, genetic and cellular levels.

Figure 2:
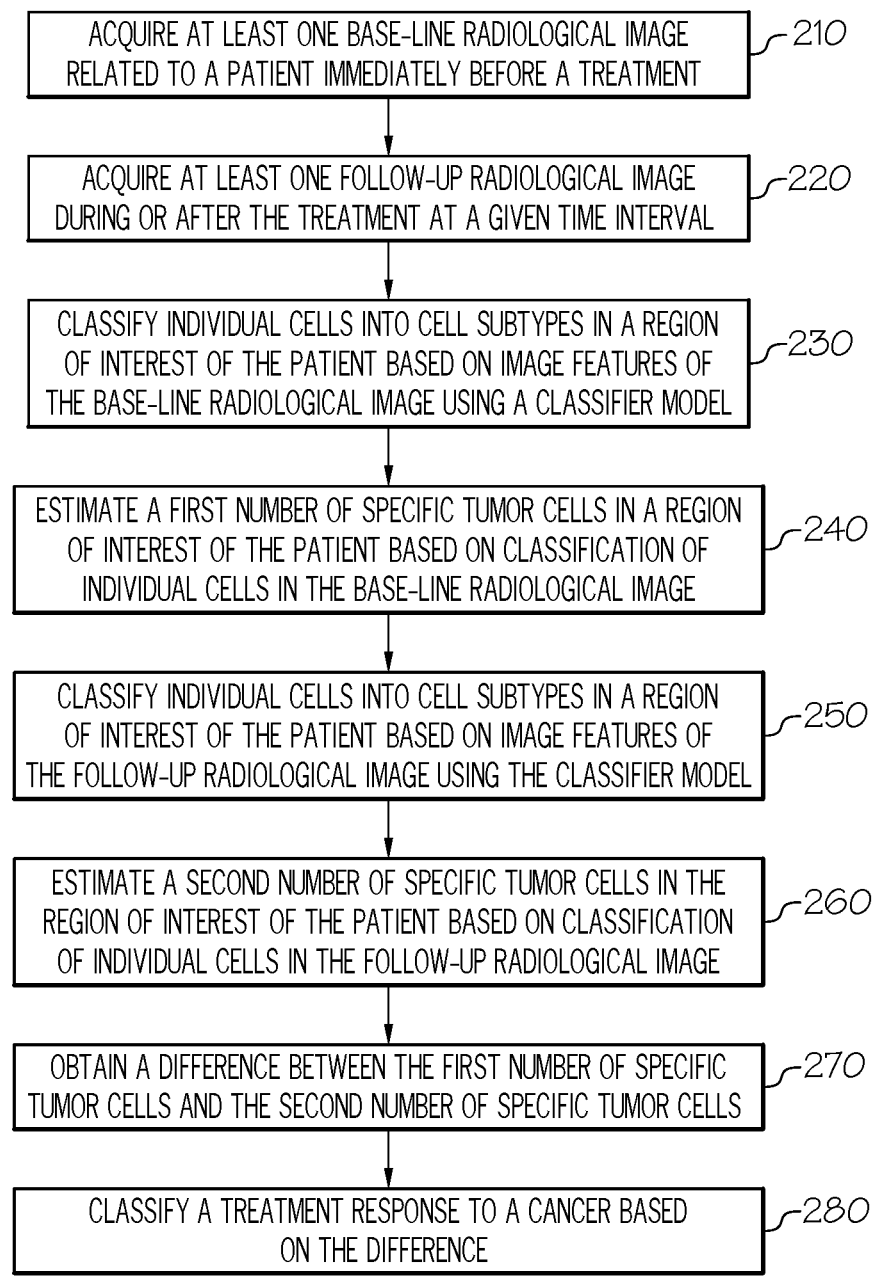
FIG. 2 depicts a flowchart illustrating example operations for assessment of therapeutic response in brain cancer, according to one or more embodiments shown and described herein.

The present disclosure provides a novel method that replaces traditional geometric measure with the measure of tumor cells to be a biomarker or metric for evaluating the treatment response. The radiomic features obtained from medical images are the first used to characterize tumor or cell alterations in volume, number and gene mutation during anti-cancer therapy. FIG. 2 shows a flowchart illustrating example operations for assessment of therapeutic response in the cancer. The method may include the following steps.

In step 210, the MRI system 10 acquires at least one base-line radiological image related to a subject (e.g., a patient) immediately before a treatment to the subject. In embodiments, the base-line radiological image may be acquired using at least one of the imaging modalities consisting of magnetic resonance imaging (MRI), computed tomography (CT), positron emission tomography (PET), X-ray, ultrasound, magnetic resonance spectroscopy (MRS), magnetic resonance spectroscopy imaging (MRSI), near-infrared (NIR) fluorescence imaging, nuclear medicine imaging, and their variations. In embodiments, the base-line radiological image may be obtained with or without administering contrast agent to the subject. For example, the base-line radiological image may be obtained by contrast enhanced imaging sequence. An exogenous or endogenous tracer may be administered into the subject before acquiring the base-line radiological image. In some embodiments, the MRI system 10 may pre-process the acquired base-line radiological image. The pre-processing may include one or more of motion correction, voxel/pixel resampling, filtering, artifact reduction, harmonization, signal normalization and image co-registration.

In step 220, the MRI system 10 acquires at least one follow-up radiological image during or after the treatment at a predetermined time interval. In embodiments, the follow-up radiological image may be acquired using at least one of the imaging modalities consisting of magnetic resonance imaging (MRI), computed tomography (CT), positron emission tomography (PET), X-ray, ultrasound, magnetic resonance spectroscopy (MRS), magnetic resonance spectroscopy imaging (MRSI), near-infrared (NIR) fluorescence imaging, nuclear medicine imaging, and their variations. In embodiments, the follow-up radiological image may be obtained with or without administering contrast agent to the subject. For example, the follow-up radiological image is obtained by contrast enhanced imaging sequence. An exogenous or endogenous tracer may be administered into a subject before acquiring the follow-up radiological image. In embodiments, the predetermined time interval may be between one week to one year after the treatment or therapy. In some embodiments, the given time internal may be shorter than one week or longer than one year.

In some embodiments, radiological images with the voxel size from 8 to 30 milliliters are acquired with PET, diffusion magnetic resonance imaging, perfusion, dynamic contrast enhanced MRI, dynamic susceptibility contrast, but not limited to, functional MRI. In some embodiments, radiological images with the voxel size from 1 to 8 milliliters are acquired with PET, diffusion magnetic resonance imaging, perfusion, but not limited to, dynamic contrast enhanced MRI, functional MRI, dynamic susceptibility contrast, $T_1$-weighted MRI, $T_2$-weighted MRI, T1/T2-weighted MRI, and their combinations. In some embodiments, radiological images with the voxel size from 0.1 to 1 milliliters are acquired with, but not limited to, PET, diffusion magnetic resonance imaging, perfusion, but not limited to, dynamic contrast enhanced Mill, functional Mill, dynamic susceptibility contrast, T1-weighted MRI, T2-weighted MRI, T1/T2- weighted MM, and their combinations. In some embodiments, the MRI system 10 may pre-process the acquired follow-up radiological image. The pre-processing may include one or more of motion correction, voxel/pixel resampling, filtering, artifact reduction, harmonization, signal normalization and image co-registration.

In step 230, the MRI system 10 classifies individual cells into cell subtypes in a region of interest of the patient based on image features of the base-line radiological image using a classifier model. In embodiments, the MRI system 10 classifies individual cells into cell subtypes such as tumor cells, inflammatory cells, normal cells, etc. In embodiments, the classifier model may be an unsupervised classification model, such as a multiple clustering model. In some embodiments, the classifier model may be a supervised classification including at least one of a fuzzy logic algorithm, a support vector machine algorithm, a regression random forest, a Gaussian mixture model, a machine learning algorithm, a deep learning algorithm. In some embodiments, the classifier model may be a biophysical model or biomarker to differentiate cell subtypes.

In step 240, the MRI system 10 estimates a first number of specific tumor cells in a region of interest of the patient based on classification of individual cells in the base-line radiological image. The volume or number of tumor cells in the region of interest before the treatment can be estimated based on image features of the base-line radiological image using an algorithm or a model, for example, a clustering algorithm. In one embodiment, the region of interest may include at least one of a region with tumor cells. In another embodiment, the region of interest may include at least one of a region with tumor cells and at least one of reference region without tumor cells.

In step 250, the MRI system 10 classifies individual cells into cell subtypes in a region of interest of the patient based on image features of the follow-up radiological image using the classifier model. In embodiments, the MRI system 10 classifies individual cells into cell subtypes such as tumor cells, inflammatory cells, normal cells, etc.

In step 260, the MRI system 10 estimates a second number of specific tumor cells in the region of interest of the patient based classification of individual cells in the follow-up radiological image. In embodiments, the MRI system 10 excludes the enhancement of image data caused by vascular and cerebrospinal fluid (CSF) and extracts the enhanced regions caused by tumor cells and inflammatory cells in the follow-up radiological image. For example, the MRI system 10 may differentiate active cancer cells from inflammatory cells in the enhanced regions. The enhanced regions after treatment may be caused by both active cancer cells and inflammatory cells. The inflammatory cells result from treatment procedure (such as radiation, chemotherapy agent, and immunotherapy agent). The enhanced regions may be segmented into two classes using statistical clustering algorithms based on the image features of the follow-up radiological image, for example, a clustering algorithm. It is noted that the tumor cells may be in either contrast enhanced regions or contrast non-enhanced regions after the administration of contrast agents. The tumor cells in the contrast enhanced regions may be caused by the leakage of contrast agents across blood-tumor barrier. The tumor cells in the contrast non-enhanced regions may be identified based on radiomics on radiological images. For example, low grade glioma may be in contrast non-enhanced regions, and the MRI system 10 may identify the low grade glioma in the contrast non-enhanced regions by applying radiomics on radiological images. In some embodiments, the tumor cells may be identified by the radiological images without contrast agents.

Each voxel or pixel of the lesion regions may be classified into a classification of tumor cells or a classification of non-tumor cells. In embodiments, the MRI system 10 may obtain the possibility of each voxel that belongs to class one (cancer cells) or class two (non-cancer cells). Further, the cancer cells may be divided into several sub-classes (such as cancer stem cells, tumor initiating cells, tumor cells) with or without intra-tumor heterogeneity. The non-cancer cells may be divided into other several subclasses (such as inflammatory cells, normal tissue cells, died cells, etc.). For example, both tumor cell and inflammatory cell may be enhanced in contrast enhanced MRI after the administration of contrast agents. It is very difficult to differentiate tumor cells from inflammatory cells according to signal enhancement in the enhanced regions. However, tumor cells and inflammatory cells can be differentiated by other image features (e.g., radiomic features) that can be obtained from either contrast enhanced MRI or other MRI modalities or image modalities. In some embodiments, tumor cells and pathological tissue with blood-tissue barrier breakdown may be identified by analyzing radiomic features of either contrast agent enhanced regions after the administration of the contrast agent or other modality images of the contrast agent enhanced regions.

In step 270, the MRI system 10 obtains a difference between the first number of specific tumor cells and the second number of specific tumor cells. In embodiments, the MRI system 10 determines variations in active cancer cells before and after the treatments based on the different between the first number of specific tumor cells before treatment and the second number of specific tumor cells after treatment. Treatment, such as cancer therapy, is performed by at least one of chemotherapy, molecular targeted therapy, immunotherapy, gene therapy, photodynamic therapy, radiation therapy, hyperthermia therapy, etc. Anticancer drugs may be used for treatment. The anti-cancer drugs include, but not limited to, all drugs approved by U.S. Food and Drug Administration (FDA) that are listed at www.cancer.gov/about-cancer/treatment/drugs/cancer-type.

In step 280, the MRI system 10 classifies a treatment response to a cancer based on the difference. In embodiments, the MRI system 10 evaluates the treatment efficacy according to the variation of tumor cells before and after the treatment obtained in step 250. The cut-off values will determine whether or not cancers in patients improve ("respond"), stay the same ("stabilize"), or worsen ("progress") during treatment. For example, 60% increase of active cancer cells may be defined as a "cancer progress", 60% decrease of the cancer cells may be defined as a "cancer response", and less than 60% variation of cancer cells may be defined as a "cancer stable". That is, the cut-off value may be 60%. In other embodiments, the cut-off value may be less than or greater than 60%. For example, the cut-off value may be adjusted according to cancer volume doubling time and interval time between baseline acquisition and treatment evaluation acquisition in order to accurately determine the treatment efficacy. Additionally, one may select a new therapy or change the previous treatment protocol (such as radiotherapy dose) when the therapy response assessment find that the treatment is not successful. If treatment response assessment indicates that the treatment is successful, one may deescalate therapy or stop the treatment early in order to reduce the side effect of anticancer therapy.

This disclosure provides following innovative features. First, the present disclosure provides more early and accurate treatment assessment. In contrast with conventional methods, the present method uses the number of tumor cells that are associated with the image features as an indicator or image biomarker for assessing response and progression of tumor treatment. The traditional image indicator for assessing therapy response is a geometric measure (e.g., tumor size and volume). Generally, the number of tumor cells based on image features changes earlier than geometric changes of the lesion occur. Thus, the present method provides insight into the therapy response at a much earlier stage, when the change of geometric measures is not detectable. Additionally, the proposed method may rapidly and accurately identify the tumor recurrence at the early stages by calculating the number of tumor cells based on image features. Thus, one can immediately stop ineffective treatment and timely change to new treatment, greatly reducing the damage of over-treatment and cost of treatment.

Second, the present method greatly reduces assessable tumor size. Most current treatment assessment or therapy response criteria requires a minimum tumor size (known as a measurable tumor), before treatment can be applied. The treatment assessment based on the current criteria requires a minimum size limit of measurable tumor. For example, the RANO criteria requires a minimum size limit of measurable brain metastases to be 5 mm. The minimum size limit of measurable tumor is limited by the spatial resolution of acquired imaging that is much less than 5.0 mm, particularly for T1-weighted and T2-weighted magnetic resonance imaging. Some studies on multiple sclerosis indicated that a minimum size limit of measurable tumor is around 3-5 folds of a voxel size. Thus, assessment criteria based on the number of tumor cells can be effective for small size brain cancer with the increasing spatial resolution. The present method pushes the treatment assessment method or therapy response criteria from the minimum measurable size of more than 5.0 mm to the detectable size of less than 3.0 mm. The present method greatly reduces the measurement variability of the response assessment, particularly for the small cancers with unregulated shapes and multiple lesions because the current response categories are defined by the proportional changes of tumor geometric measures.

Third, the present method is more flexible for tumor size, shape, and multiple tumor lesions. Generally, existing treatment assessment ignores the effect of treatment on the tumor size of less than measurable tumor. As a result, it is very difficult to make accurate assessment of therapy response. The proposed method can evaluate the treatment effect of all detectable tumors (around 3-5 voxels or a pixel size) which size is much less than the size of measurable tumors. The accuracy and precision of the present method is almost independent of tumor size, shape and lesion numbers.

Fourth, the present method provides effective identification both pseudo-progression and pseudo-response. The present method integrates machine learning with image feature to quantify the number of cells over time during tumor treatment for conducting fast and accurate treatment assessments. For example, the present method may use radiomic features and mathematical models to differentiate cancer cells and inflammatory cells, and identify the pseudo-progression caused by the inflammatory cells. In contrast, it is very difficult for the conventional treatment assessment or therapy response criteria to identify pseudo-progression or pseudo-response. For example, the Macdonald criteria, for treatment response assessment of high-grade gliomas provided an objective radiologic assessment of tumor response, based on the product of the maximal cross-sectional enhancing diameters as the primary tumor measure may not be able to differentiate pseudo-progression or pseudo-response from true response. However, various factors, such as treatment-related inflammation, seizure activity, postsurgical changes, ischemia, sub-acute radiation effects, and radiation necrosis, can lead to an increased enhancement, creating a pseudo-progression, thereby deteriorating accurate treatment assessment. Moreover, the decrease in contrast enhancement (i.e., pseudo-response) can be often observed during antiangiogenic treatments such as bevacizumab. The present method holds a great potential to differentiate the pseudo-progression and pseudo-response from true responses by the quantification of cancer cells during or after the anti-cancer therapy.

Fifth, the present method provides ability for precision medicine. The treatments often introduce intra-tumor heterogeneity. In the era of precision medicine, a reliable and real-time assessment of the effectiveness of new therapies at molecular, genetic and cellular levels is of outstanding importance. Conventional treatment assessment methods or therapy response criteria do not provide cancer biology information at molecular, genetic and cellular levels. Thus, it is very difficult to accurately assess targeted therapies. For example, it is very difficult to differentiate the unsuccessful targeted treatment caused by an ineffective treatment method from gene mutation during the therapies. The present method may characterize the change in both the number of cells and intra-tumor heterogeneity at molecular, genetic and cellular levels. It will be available for precision medicine and may be able to make a decisive contribution for a timely targeted therapy.

Sixth, the present method provides more generality for image modalities and different treatment methods. Conventional treatment assessments and therapy response criteria depend on the image modalities and treatment methods, such as RECIST, iRECIST, and PET Response Criteria in Solid Tumors (PERCIST). The obtained concepts and methods can be extended to different image modalities and different treatment methods. In summary, the present method can provide a non-invasive, fast, reliable, accurate, reproducible, general therapy response assessment of cancer at the early stages. It may help the clinicians in estimating the effectiveness of different therapies and choosing the best strategy. As a result, it will greatly improve cancer patient management and outcomes. It can also speed up the development of anti-cancer drugs, save the expense, and improve the successful rate of the anti-cancer drugs.

Seventh, the present method may detect the cancer recurrence early and accurately. Recurrence is major concern for subjects being treated for cancer. For example, recurrence occurs in approximately 50% of patients with non-small cell lung cancer. Currently, cancer recurrence is not detected until the cancer has grown to a size that is detectable. This delay may complicate treatment, reduce a patient's treatment options, and result in a poorer prognosis for the patient. In some embodiments, the present method and system may detect recurrence early and accurately.

Methods for determining cancer therapy response include invasive methods, and minimally invasive or non-invasive methods. Among these methods, non-invasive imaging methods are promising and desirable. The conventional image methods or response criteria based on geometric measure is not sensitive to the change of the number of cancer cells and biology heterogeneity. The conventional methods cannot provide a rapid and accurate characterization of anti-cancer therapy. However, the present method and system overcome the drawback of conventional methods or response criteria and provide a non-invasive, fast, accurate and effective description of therapy responses at molecular, genetic and cellular levels.

The present method provides the following technical advantages. First, the present method provides immediate and accurate indications of tumor response, thereby eliminating the current lengthy delays in assessing treatment response. As a result, the present method greatly improves the cancer patient management and outcomes.

Second, the present method provides early therapy evaluation because it does not require minimum measurable tumor size of 5.0 mm. The detectable tumor size is around 3-5 voxel sizes (e.g., less than 3.0 mm for most contrast agent enhanced MRI). In some embodiments, a diameter of at least one of the measurable region of interests (e.g., a region including tumor cells) acquired with PET, diffusion magnetic resonance imaging, perfusion, but not limited to, dynamic contrast enhanced MRI, functional MRI, dynamic susceptibility contrast, T1-weighted MRI, T2-weighted MRI, T1/T2-weighted MRI, and their combinations, may be less than 5.0 mm. In some embodiments, a diameter of at least one of the measurable region of interests may be less than 1.0 mm. In other embodiments, a diameter of at least one of the measurable region of interests may be less than 0.2 mm.

Third, the present method easily differentiates pseudo-progression and pseudo-response from true response. The conventional existing response criteria and assessment method for treatment response recommends delayed time to be around 3 months for radiotherapy to 6 months for immunotherapy in order to reduce the effect of pseudo-progression so that the accurate treatment effect can be identified. The delayed time is relatively long, compared to the survival time of most of brain tumor (around 12 months). On the other hand, the present method shortens the delayed time to differentiate the pseudo-progression and true progression, and then changes the patient management. It is crucial to recognize true progression in a timely manner, and consideration should be given to additional or alternative therapies as early as possible, in order to prevent side effects from prolonged treatment. These treatment-associated adverse events impact on the patients' quality of life.

Fourth, the present method monitors the therapy response at molecular, genetic and cellular levels and provides a potential personalized medicine for cancer patients. For example, conventional treatment response assessment methods and systems do not accurately and efficiently determine personalized absorbed dose estimates of targeted radiotherapy. The present method accurately catches the change of tumor cells in real-time and provides a potential for personalized treatment and improve the efficacy and reducing toxicity of cancer therapy. For example, an improved understanding of the genomic architecture of breast cancers can lead to a transition from chemotherapy to genotype-guided treatment approaches.

Fifth, the present method provides a timely and accurate treatment evaluation of the development of both anti-cancer drugs and anti-therapies. As a result, the present method greatly reduces the time and expense of anti-therapies, and increases successful rate of anti-cancer drug development.

Sixth, the present method provides a more general method for all anti-cancer therapies. Current assessment methods and therapy response criteria strongly depend on therapeutic methods. For example, there are RECIST for chemotherapy and radiation therapy, and iRECIST for immunotherapy.

Seventh, the present method detects tumor recurrence in an early stage. Intra-tumor heterogeneity only impacts a small fraction of the cells with resistant mutations. The larger the tumor lesion, the more likely that such resistant tumor cells exist. Thus, early detection of tumor recurrence after a therapy may be more likely to be successful than treatment of larger tumor recurrence with the optimal and alternative treatment. Eight, the present method provides less dependence on the image modalities. For example, RECIST criteria for assessing tumor therapy response bases on the geometry metric of a solid tumor, which is sequence-dependent. At most case, the geometry metric measured by spin echo sequence is different from that measured by gradient echo sequence because the spin echo is sensitive to edema. Most image modalities, such as MRI, PET and CT, have a typical spatial resolution of millimeter, and only provide only a volume average and non-specific reflection of the pathological change at molecular, genetic and cellular levels in in vivo therapy response.

The progression of these techniques provides a potential to characterize the cancer biology properties inside a cancer using high resolution images, particularly when the cancer size is comparable to the voxel size of the images.

In contrast with conventional methods that apply AI to radiological images for assessing therapy responses at macroscopic level, the present method assesses the therapy response at microscopic level using AI and radiological images. More specially, the present method uses machine learning and/or deep learning techniques to characterize the changes in cells with or without genetic information during or after the anti-cancer therapy, including normal tissue cells, uncontrollable cancer cells, inflammation cells, necrosis cells, etc.

Figure 3:
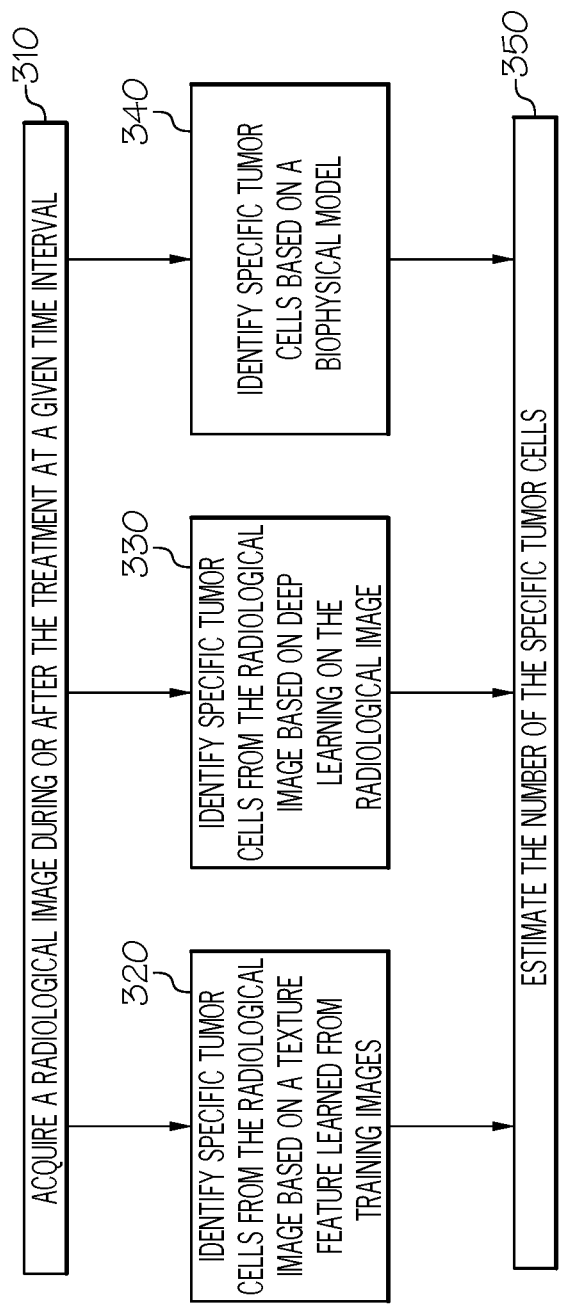
FIG. 3 depicts a flowchart for estimating the number of specific tumor cells in a radiological image according to one or more embodiments shown and described herein.

FIG. 3 depicts a flowchart for estimating the number of specific tumor cells in a radiological image according to one or more embodiments shown and described herein.

In step 310, the MRI system 10 acquires a radiological image during or after the treatment at a predetermined interval. Once the radiological image is acquired, the MRI system identifies specific tumor cells in the radiological image using various methods, for example, three different methods described in steps 320, 330, 340.

As one of the methods for identifying the specific tumor cells, in step 320, the MRI system 10 may identify specific tumor cells from the radiological image based on a texture learned from training images. For example, the texture may be learned based on machine learning on images that include features for the specific tumor cells. The details of the machine learning will be described below with reference to FIG. 4.

As another method for identifying the specific tumor cells, in step 330, the MRI system 10 may identify specific tumor cells from the radiological image based on deep learning on the radiological image. The details of the machine learning will be described below with reference to FIG. 7.

As another method for identifying the specific tumor cells, in step 340, the MRI system 10 may identify specific tumor cells from the radiological image based on application of a biophysical model on the radiological image. The biophysical model may be a simulation of a biological system using mathematical formalizations of the physical properties of that system. Such models can be used to predict the influence of biological and physical factors on complex systems. For example, the uncontrolled division of cells in a tumor region requires acquisition of necessary nutrients from a frequently nutrient-poor environment, leading to increased blood volume. As a result, dynamic susceptibility contrast MRI indicates measures of cerebral blood volume are significantly higher in a tumor region compared with a non-tumor region. Thus, the cerebral blood volume may be a marker to quantify the tumor cells.

The objective of these methods in steps 320, 330, 340 is to uncover the relationship between image features and tumor cells by mathematical or statistical models in order to quantify the change in tumor cells over time during or after anti-cancer therapy.

In step 350, the MRI system 10 may estimate the number of the specific tumor cells based on the identification of specific tumor cells in steps 320, 330, or 340.

In embodiments, a support vector machine with radiomic features may be employed to predict recovery outcome in patients with Intracerebral hemorrhage (ICH). The following schema for fluid-attenuated inversion recovery (FLAIR) MRI data preprocessing may be conducted: 1) skull stripping (comprises the process of removing skull, extra-meningeal and non-brain tissues from the MRI data); 2) bias field correction (removing the signal intensity inhomogeneity mainly caused by radiofrequency coils); and 3) intensity normalization (reducing the variations of signal intensity and contrast across subjects). After the preprocessing, 3D U-Net convolutional neural network model may be implemented to segment hemorrhages. Then, 105 radiomics features from the segmented hemorrhages may be extracted using pyRadiomics pipeline, including 13 geometric features (e.g., volume, surface area, compactness, maximum diameter, sphericity), 18 histogram features (e.g., variance, skewness, kurtosis, uniformity, entropy), 14 texture features from the Gray-Level Dependence Matrix, 23 texture features from the Gray-Level Co-Occurrence Matrix, 16 texture features from the Gray-Level Run-Length Matrix, 16 texture features from the Gray-Level Size Zone Matrix, and 5 texture features from the Neighborhood Gray-Tone Difference Matrix. To prevent model overfitting, feature dimensionality using least absolute shrinkage and selection operator (LASSO) algorithm may be reduced. The LASSO algorithm minimizes the residual sum of squares and poses a constraint to the sum of the absolute values of the coefficients being less than a constant. The LASSO algorithm constructs a linear model, which penalizes the coefficients with an L1 penalty, such that some coefficients can be shrunk to zero. Features with non-zero coefficients were selected by the LASSO. Based on the 54 LASSO-selected radiomics features, a support vector machine (SVM) model with a polynomial kernel to conduct two-class classification is generated. Using a 5-fold cross-validation, the classification diagnostic performance of our SVM models may be established, including accuracy, sensitivity, specificity, and area under the receiver operating characteristic curve. As a result, the present method can correctly identify patients likely to have unfavorable outcomes with an accuracy of 80.8% (95% confidence interval: 78.9%, 82.8%), AUC of 0.81 (95% confidence interval: 0.79, 0.83), sensitivity of 88.2% (95% confidence interval: 86.1%, 90.4%) and specificity of 72.7% (95% confidence interval: 69.0%, 76.4%).

Figure 4:
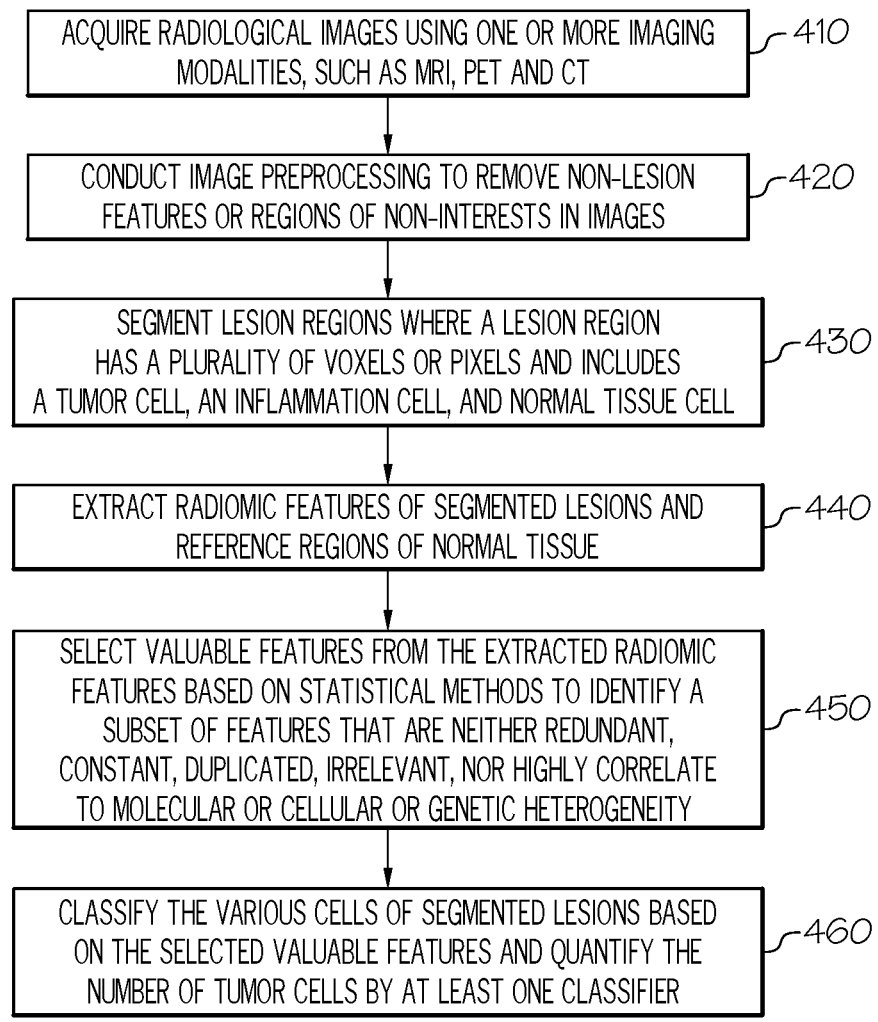
FIG. 4 depicts a flowchart for classifying and quantifying tumor cells by integrating image features and machine learning algorithms according to one or more embodiments shown and described herein.
Figure 5A:
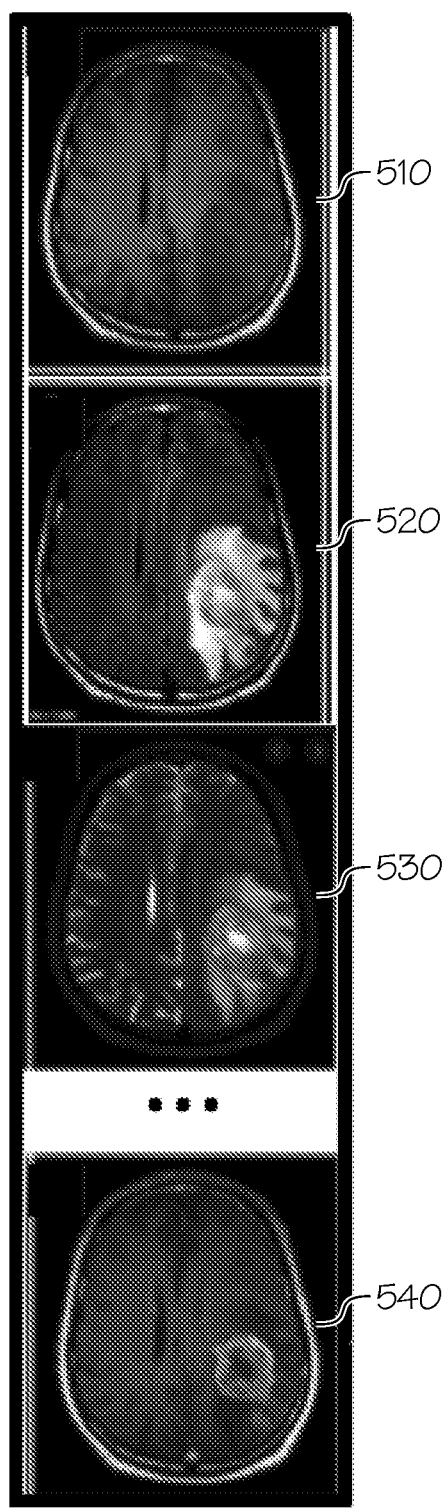
FIG. 5A depicts exemplary radiological images, according to one or more embodiments shown and described herein.
Figure 5B:
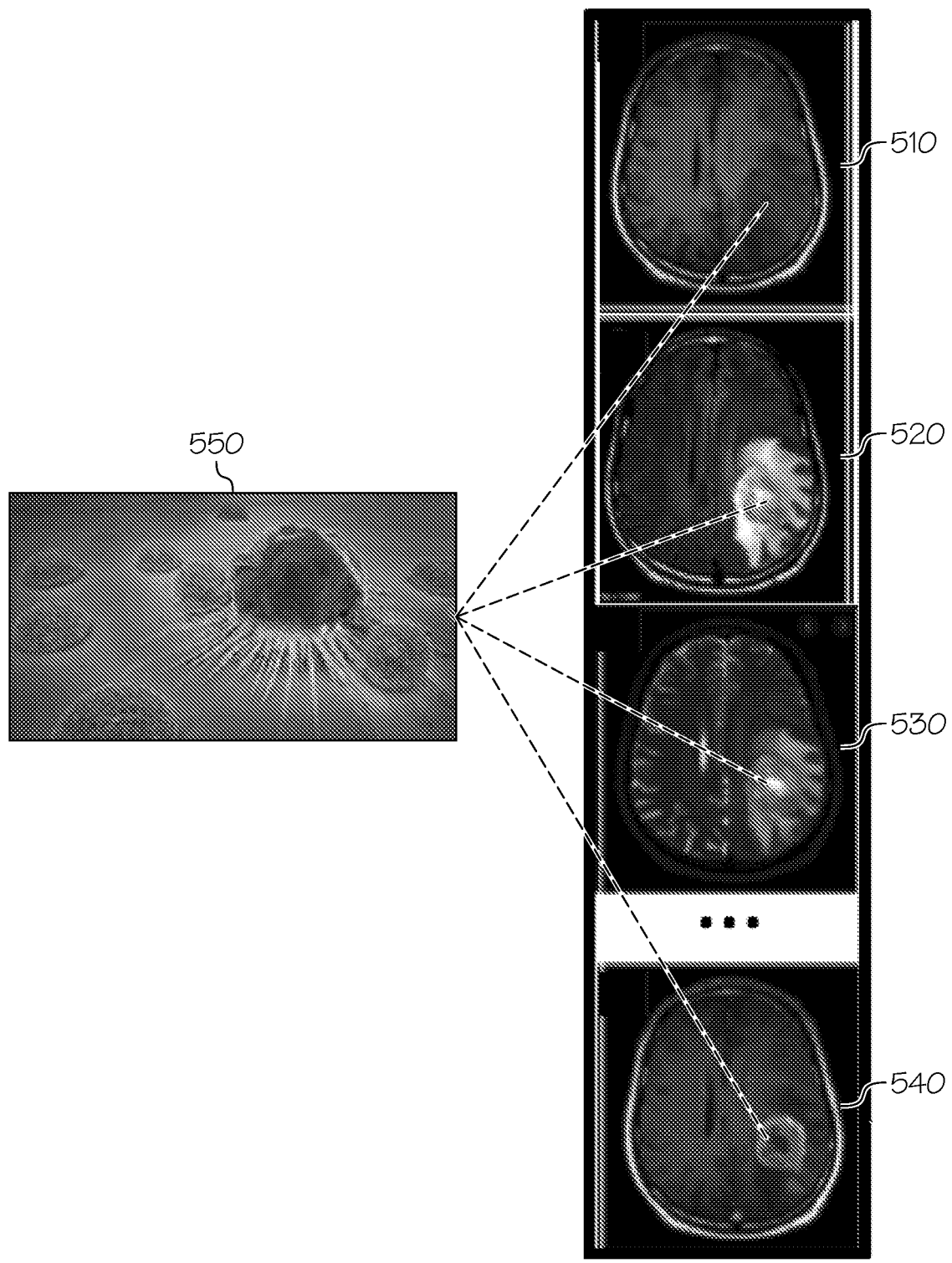
FIG. 5B depicts exemplary radiological images with tumor cell or normal cells, according to one or more embodiments shown and described herein.

FIG. 4 depicts a flowchart for classifying and quantifying tumor cells by integrating image features and machine learning algorithms according to one or more embodiments shown and described herein. In step 410, the MRI system 10 acquires radiological images using one or more imaging modalities, such as MRI, PET and CT. For example, the MRI system 10 acquires multi-modal images including an image 510 (Pre-T1-weighted image), an image 520 (Pre-T2-weighted fluid-attenuated inversion recovery image), an image 530 (Pre-T2-weighted image), and an image 540 (post-contrast T1-weighted image) in FIG. 5A. As illustrated in FIG. 5B, each of the images 510, 520, 530, 540 may include a segmented region that includes cancer cells 550.

In step 420, the MRI system 10 conducts image preprocessing to remove non-lesion features or regions of non-interests in images.

In step 430, the MRI system 10 segments lesion regions (e.g. tumor, edema, necrosis, etc.) where a lesion region has a plurality of voxels or pixels and includes tumor cells, inflammation cells, and normal tissue cells.

In step 440, the MRI system 10 extracts radiomic features of the segmented lesion regions and reference regions of normal tissue. The various methods, such as PyRadiomics, MaZda, LifeX, and Z-Rad, may be used to extract the radiomic features, where the features include, but are not limited to, size and shape based-features, descriptors of the image intensity histogram, descriptors of the relationships between image voxels (e.g., gray-level co-occurrence matrix, run length matrix, size zone matrix, and neighborhood gray tone difference matrix derived textures), and textures extracted from filtered images, and fractal features. A large number of extracted features may be used to distinguishing the parameters relevant to molecular or cellular or genetic heterogeneity.

In step 450, the MRI system 10 selects valuable features from the extracted radiomic features based on statistical methods to identify a subset of features that are neither redundant, constant, duplicated, irrelevant, nor highly correlate to molecular or cellular or genetic heterogeneity. At least one feature extracted from the segmented lesion regions may represent features related to tumor cells and/or gene mutations. Additionally, at least one feature extracted from reference regions may correspond to features related to normal tissue cells. For example, the features of tumor cells correspond to high entropy, compared with the features of normal tissue cells.

Figure 6:
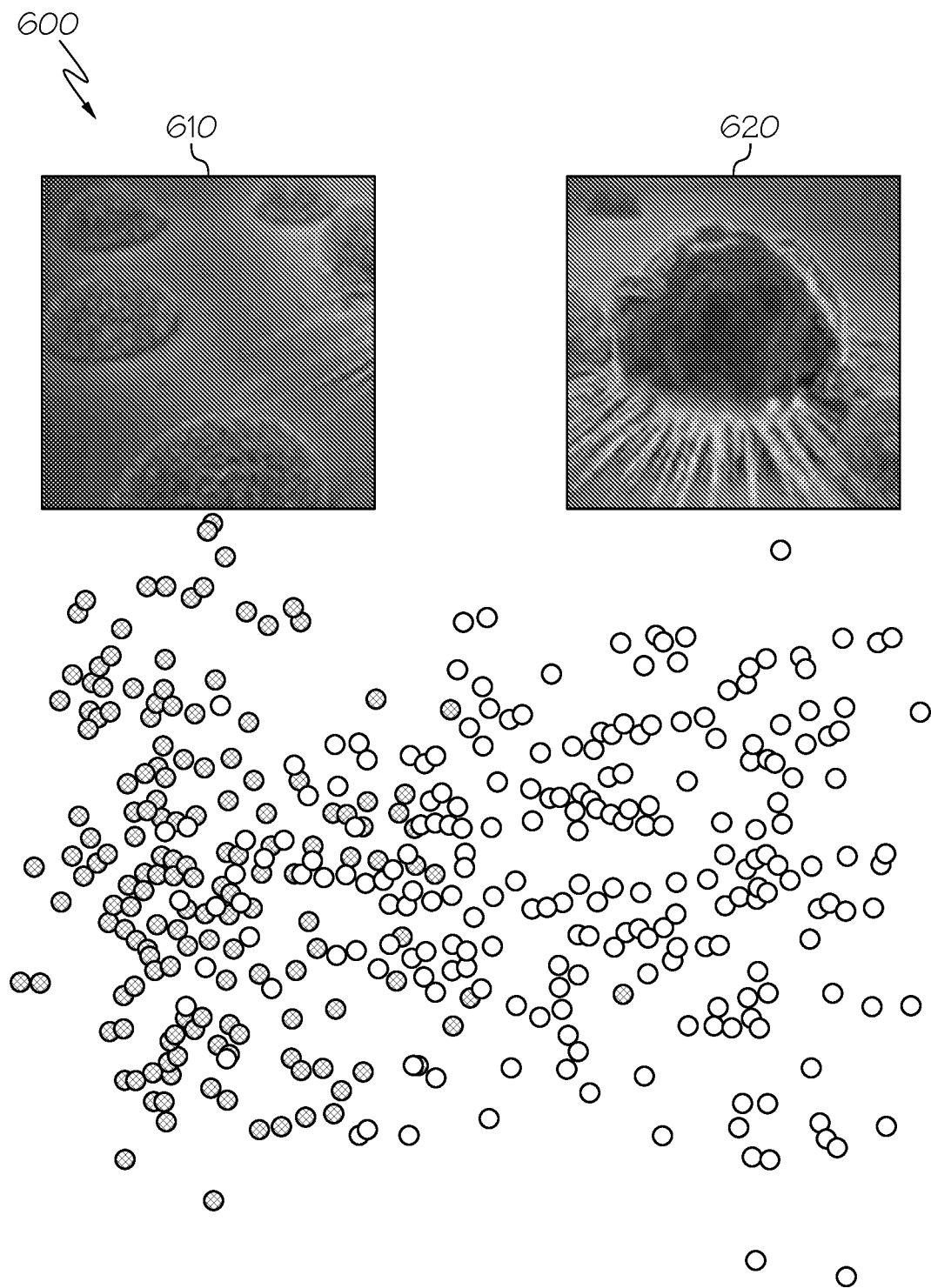
FIG. 6 depicts a group of cells classified as tumor cells or normal cells.

In step 460, the MRI system 10 classifies the various cells of segmented lesion regions based on the selected valuable features and quantifies the number of tumor cells by at least one classifier. For example, FIG. 6 depicts a group of cells 600. The MRI system 10 may classify the group of cells 600 into either tumor cells 610 or normal cells 620.

Most recent years, deep learning has emerged as one of the most promising tools for abnormality detection, discriminative biomarkers identification and image classification. Traditional machine learning requires explicit feature extraction to reduce data complexity. Such approaches are often less adequate in properly modeling high-dimensional data. Alternatively, deep learning enables the extraction of biologically meaningful features and revealing discriminative information from complex and high-dimensional data automatically via self-learning.

Figure 7:
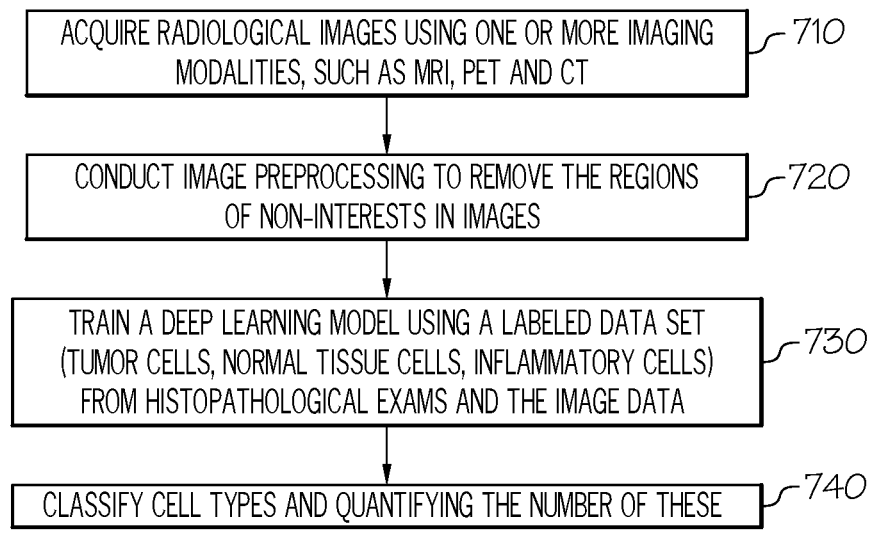
FIG. 7 depicts a flowchart for classifying and quantifying tumor cells by a deep learning model according to one or more embodiments shown and described herewith.

FIG. 7 depicts a flowchart for classifying and quantifying tumor cells by a deep learning model according to one or more embodiments shown and described herewith.

In step 710, the MRI system 10 acquires radiological images using one or more imaging modalities, such as MRI, PET and CT. For example, the MRI system 10 acquires radiological images 510, 520, 530, 540 in FIG. 5A In step 720, the MRI system 10 conducts image preprocessing to remove the regions of non-interests in radiological images.

Figure 8:
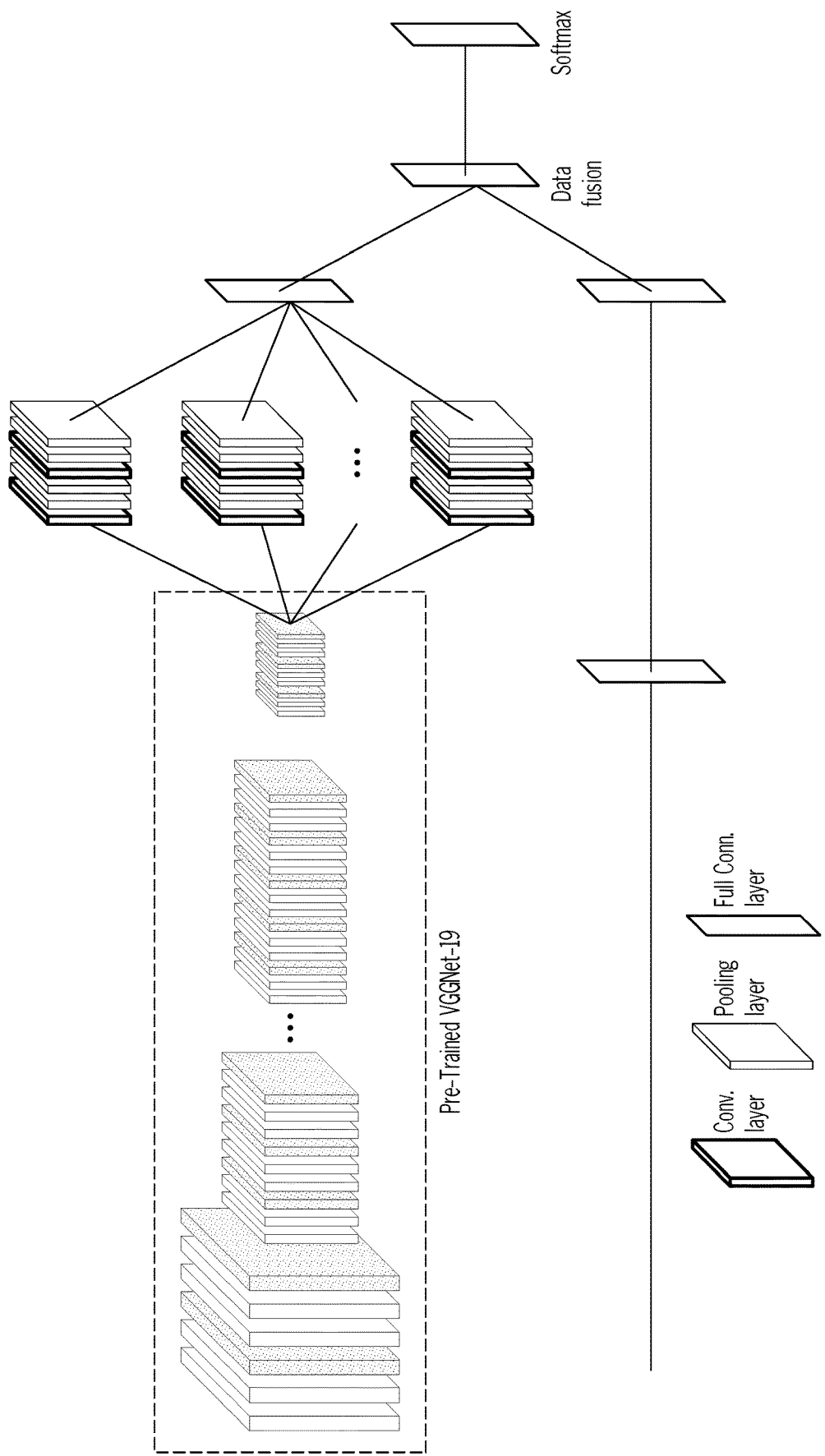
FIG. 8 depicts an exemplary deep learning model.

In step 730, the MRI system 10 trains a deep learning model using a labeled data set (tumor cells, normal tissue cells, inflammatory cells) from histopathological exams and the preprocessed radiological images. FIG. 8 depicts an exemplary deep learning model.

In step 740, the MRI system 10 classifies cell types of the cells in the radiological images using a classifier of the deep learning model and quantifying the number of classified cells. In some embodiments, the classifier is an unsupervised clustering algorithm/model, which can identify multiple cell types with or without genetic heterogeneity in high dimensional image feature space. In some embodiments, the classifier is a supervised classification algorithm/model, which is trained on a set of image features derived from acquired high resolution images of preselected patient populations or simulated images with the specific tumor cells, normal tissue cells, etc. The trained model is fine-tuned and validated on a separate independent set of images. Finally, another independent set of images is used to test the model and report final statistical results. It is noted that each of the three sets of images should be independent, without overlap. Also, the inclusion and exclusion criteria for the dataset, in addition to the justification for removing any outlier, should be explained.

In embodiments, a deep transfer learning model may be utilized to accurately predict clinical outcome in patients with ICH (e.g., at 3 months) using the integration of clinical and FLAIR imaging data. The deep learning model may include two separate input channels, one for imaging and the other for clinical data. To extract high-level discriminative imaging features in imaging channel, a module with 24 layers may be designed by reusing the weights of a pre-trained VGG-19 model ($1^{st}$ to $21^{st}$ layers), and then the weights of two additional convolutional layers with [64, 128] neurons and 3×3 filters and one fully-connected layer with 64 neurons is trained. For each patient, the model analyzed n=8 slices containing the entire hemorrhagic lesion. For the clinical channel, one fully-connected layers with 64 neurons was applied to learn the discriminative features from the clinical data. Finally, a fully connected fusion layer with 64 neurons was applied to integrate the extracted discriminative information from both imaging and clinical data. A two-way softmax classifier was then utilized to identify the patients likely to have unfavorable outcomes. Rotation and shift-based data augmentation strategy was implemented to increase the training samples by 10 times (but not testing samples). As a result, the present model may correctly identify patients likely to have unfavorable outcomes with an AUC of 0.87 (95% confidence interval: 0.86, 0.89).

In some embodiments, the present method and system assess therapy response in different types of tumors, such as prostate cancer, malignant pleural mesothelioma, non-small cell lung cancer, gastrointestinal stromal tumor, soft tissue sarcoma, neuroendocrine tumors, and disseminated pediatric malignant, primary brain tumor, and their brain metastases.

In some embodiments, the treatment of cancer or cancer includes surgery, chemotherapy, but not limit to, radiation therapy, hormonal therapy, immunotherapy, targeted therapy, stem cell transplants, anti-cancer drug, precision medicine and their combinations.

In some embodiments, the specific tumor cells can be differentiated using the image features that are extracted by acquired images. For example, active cancer cell and pathological tissue with blood-tissue barrier breakdown may be identified by analyzing contrast agent enhanced regions after the administration of the contrast agent.

In some embodiments, the methods described herein may include the quantification of a particular cell type in region of interests. In these embodiments, the methods include differentiate the presence of one or more cancer cells in the region of interests, where the differentiation is made based on the radiomic feature derived from the obtained image data. In another embodiment, the clinicians or other users may identify or assess a change of the cancer cells over time through two or more images This disclosure describes method and system to assessment of therapeutic response in cancer using magnetic resonance imaging (MRI) herein. It should be understood that the proposed method may be available for other image modalities to assessment therapy response, such as a positron emission tomography (PET) apparatus, a computed tomography (CT) apparatus, and a single positron emission computed tomography (SPECT) apparatus. Additionally, it should be understood that this disclosure should include all MRI image modalities, such as T1-weighted imaging, T2-weighted imaging, diffusion, diffusion tensor imaging, susceptibility-weighted imaging, perfusion-weighted imaging, chemical shift imaging, intra-voxel incoherent motion, but not limit to, and their combinations with and/or without the administration of contrast agent. As a result, this disclosure provides non-invasive, safer, faster, accurate, earlier, more effective method and system for assessing therapy response in all research, drug development and clinical practices.

Optionally, image modalities include 2 dimensional or 3 dimensional imaging acquisition in space. Optionally, the region of interest may include at least one of a lesion, a landmark, a texture, or a feature of interest.

The invention claimed is:

1. A method for assessing a patient response to a cancer treatment, the method comprising:
    acquiring at least one base-line radiological image related to a patient immediately before a treatment;
    acquiring at least one follow-up radiological image during or after the treatment at a predetermined time interval;
    classifying individual cells into cell subtypes in a region of interest of the patient based on image features of the base-line radiological image using a classifier model;
    estimating a first number of specific tumor cells in the region of interest of the patient based on classification of individual cells in the base-line radiological image;
    classifying individual cells into cell subtypes in the region of interest of the patient based on image features of the follow-up radiological image using the classifier model;
    estimating a second number of specific tumor cells in the region of interest of the patient based on classification of individual cells in the follow-up radiological image;
    obtaining a difference between the first number of specific tumor cells and the second number of specific tumor cells; and
    classifying a treatment response to a cancer based on the difference.

2. The method of claim 1, wherein the cancer is a solid cancer, and
    wherein the solid cancer is primary brain tumors or brain metastases.

3. The method of claim 1, wherein the specific tumor cells have different characterization at molecular or genetic levels from other cells, the characterization including one or more of molecular types, gene expression, or mutations.

4. The method of claim 1, further comprising pre-processing the at least one base-line radiological image and the at least one follow-up radiological image,
    wherein the pre-processing includes one or more of motion correction, artifact reduction, harmonization, signal normalization and image co-registration.

5. The method of claim 1, wherein the base-line radiological image and the follow-up radiological image are acquired using at least one of the imaging modalities consisting of magnetic resonance imaging (MRI), computed tomography (CT), positron emission tomography (PET), X-ray, ultrasound, magnetic resonance spectroscopy (MRS), magnetic resonance spectroscopy imaging (MRSI), near-infrared (NIR) fluorescence imaging, nuclear medicine imaging, and their variations.

6. The method of claim 1, wherein the base-line radiological image and the follow-up radiological image are acquired after administration of contrast agent.

7. The method of claim 1, wherein the classifier model is an unsupervised classification model including a multiple clustering model.

8. The method of claim 1, wherein the classifier model is a supervised classification comprising at least one of a fuzzy logic algorithm, a support vector machine algorithm, a regression random forest, a Gaussian mixture model, a machine learning algorithm, a deep learning algorithm.

9. The method of claim 1, wherein the classifier model is a biophysical model or biomarker to differentiate the cell subtypes.

10. The method of claim 1, wherein estimating the first number of specific tumor cells or estimating the second number of specific tumor cells includes detecting the presence of tumor cells using image features that are associated with cancer biology including, blood-brain barrier disruption, hypoxia, vasogenic edema, heterogeneity, and inflammation.

11. The method of claim 1, wherein the given predetermined time interval is between one week to one year after the treatment or therapy.

12. The method of claim 1, wherein the specific tumor cells are generated from one of the following group consisting of lung cancer, ovarian cancer, melanoma, breast cancer, prostate cancer, lung cancer, pancreatic cancer, colon cancer, hepatic cancer, primary brain cancer and brain metastases.

13. The method of claim 1, wherein the image features include at least one of size and shape based-features, descriptors of the image intensity histogram, descriptors of the relationships between image voxels including a gray-level co-occurrence matrix (GLCM), run length matrix (RLM), size zone matrix (SZM), and neighborhood gray tone difference matrix (NGTDM) derived textures, textures extracted from filtered images, and fractal features.

14. The method of claim 1, wherein the measurable region of interest includes one or more tumor lesions.

15. The method of claim 1, wherein a diameter of at least one of the measurable region of interests is less than 5.0 mm.

16. The method of claim 1, wherein a diameter of at least one of the measurable region of interests is less than 1.0 mm.

17. The method of claim 1, wherein a diameter of at least one of the measurable region of interests is less than 0.2 mm.

18. The method of claim 1, further detecting or diagnosing cancer recurrence at an early stage based on increased tumor cells in one or more regions of interest after treatment that were previously without tumor cells.

19. The method of claim 1, wherein the treatment response indicates an increase, a stagnation or a non-substantial decrease in an amount of specific tumor cells.

20. A system for contrast enhancement, the system comprising:

a receiver configured to:
   acquire at least one base-line radiological image related to a patient immediately before a treatment; and
   acquire at least one follow-up radiological image after the treatment at a predetermined time interval; and
a processor configured to:
   classify individual cells into cell subtypes in a region of interest of the patient based on image features of the base-line radiological image using a classifier model;
   estimate a first number of specific tumor cells in a region of interest of the patient based on classification of individual cells in the base-line radiological image;
   classify individual cells into cell subtypes in the region of interest of the patient based on image features of the follow-up radiological image using the classifier model;
   estimate a second number of specific tumor cells in the region of interest of the patient based on classification of individual cells in the follow-up radiological image;
   calculate a difference between the first number of specific tumor cells and the second number of specific tumor cells; and
   classify a treatment response to a cancer based on the difference.

* * * * *